(12) United States Patent
Zhou et al.

(10) Patent No.: US 7,842,174 B2
(45) Date of Patent: Nov. 30, 2010

(54) ELECTROCHEMICAL CHIP WITH MINIATURIZED SENSOR ARRAY

(75) Inventors: Anhong Zhou, Logan, UT (US); Huifang Dou, Logan, UT (US)

(73) Assignee: Utah State University, North Logan, UT (US)

( * ) Notice: Subject to any disclaimer, the term of this patent is extended or adjusted under 35 U.S.C. 154(b) by 632 days.

(21) Appl. No.: 11/761,916

(22) Filed: Jun. 12, 2007

(65) Prior Publication Data

US 2008/0087544 A1    Apr. 17, 2008

Related U.S. Application Data

(60) Provisional application No. 60/813,299, filed on Jun. 12, 2006.

(51) Int. Cl.
G01N 27/26 (2006.01)
G01N 27/00 (2006.01)
G01R 19/00 (2006.01)

(52) U.S. Cl. ............... 204/406; 204/400; 324/693; 324/700; 324/76.11; 422/82.01

(58) Field of Classification Search ............ 73/86; 324/71.2, 693, 700, 425, 432, 444, 76.11; 204/400–435; 422/82.01
See application file for complete search history.

(56) References Cited

U.S. PATENT DOCUMENTS

| | | | |
|---|---|---|---|
| 4,225,410 A | | 9/1980 | Pace |
| 4,986,271 A | * | 1/1991 | Wilkins ............... 600/347 |
| 5,063,361 A | * | 11/1991 | Smith et al. ............ 332/103 |
| 5,208,646 A | * | 5/1993 | Rogers et al. ........ 356/139.09 |
| 5,316,633 A | * | 5/1994 | Sakai et al. ............ 205/777 |
| 5,708,687 A | * | 1/1998 | Powell et al. ............ 375/376 |
| 6,143,667 A | * | 11/2000 | Marsh ............... 438/740 |
| 6,147,851 A | * | 11/2000 | Anderson ............... 361/107 |
| 6,906,524 B2 | | 6/2005 | Chung et al. |
| 7,084,641 B2 | | 8/2006 | Brederlow et al. |

(Continued)

OTHER PUBLICATIONS

Romero, Mario R. et al., "A Computer-Controlled Battery-Powered Micropotentiostat," Departamento de Quimica y Fisica, Universidad Nacional de Rio Curato, Ruta 8, Km 601, 5800, Rio Curato, Argentina, Oct. 25, 1999, pp. 53-58, vol. 12, 2000 John Wiley & Sons, Inc., Lab Robotics and Automation (LRA).

(Continued)

Primary Examiner—Nam X Nguyen
Assistant Examiner—Susan Thai

(57) ABSTRACT

A handheld sensor device is provided for measuring an ion concentration in a solution. The solution is in an electrochemical cell that includes a counter electrode, a working electrode, and a reference electrode. The sensor includes a control amplifier configured to provide a current through the counter electrode and the working electrode so as to maintain a predetermined voltage between the working electrode and the reference electrode. The sensor also includes a current amplifier configured to measure the current provided through the counter electrode and the working electrode. In one embodiment, the sensor also includes a direct digital frequency synthesizer (DDFS) including a phase accumulator. The DDFS is configured to selectively generate a waveform specified by an electrochemical technique such as square wave voltammetry, cyclic voltammetry, linear sweep voltammetry, differential-pulse polarography, normal-pulse polarography, or other known electrochemical techniques. An example microelectrode array usable with the handheld sensor is also provided.

30 Claims, 23 Drawing Sheets

U.S. PATENT DOCUMENTS

| | | | |
|---|---|---|---|
| 7,189,314 | B1 | 3/2007 | Pace et al. |
| 2003/0169618 | A1* | 9/2003 | Lindsey et al. ............... 365/151 |
| 2005/0067279 | A1 | 3/2005 | Chen et al. |
| 2005/0112544 | A1 | 5/2005 | Xu et al. ........................ 435/4 |

OTHER PUBLICATIONS

Gore, Amit et al., "A Multichannel Femtoampere-Sensitivity Potentiostat Array for Biosensing Applications," Nov. 2006, pp. 2357-2363, vol. 53, No. 11, 2006 IEEE Transactions on Circuits and Systems—I: Regular Papers, Digital Object Identifier (DOI) 10.1109/TCSI.2006.884432.

Wollenberger, U. et al., "Biosensors for analytical microsystems," Microsystem Technologies, 1995, p. 75-83, ISSN: 0946-7076, vol. 1, Issue 2, Springer-Verlag 1995, DOI 10.1007/BF01624467.

Wittstock, Gunther, "Sensor arrays and array sensors," Dec. 8, 2001, pp. 16-17, ISSN 1618-2642, vol. 372, Issue 1, Analytical and Bioanalytical Chemistry, Springer-Verlag 2001, DOI 10.1007/s00216-001-1149-y.

Huang, Chengjun et al., "Design and Fabrication of an Automated Microchip-Based Cell Separation Device," 2006, pp. 763-778, vol. 40, Issue 4, Analytical Letters, Taylor & Francis Group, LLC, ISSN 0003-2719 print/1532-236X online, DOI 10.1080/00032710601017896.

Ayers, Sunitha, et al., "Design of a CMOS Potentiostat Circuit for Electrochemical Detector Arrays," Apr. 2007, pp. 736-744, vol. 54, No. 4, 2007 IEEE Transactions on Circuits and Systems—I: Regular Papers, DOI 10.1109/TCSI.2006.888777.

Zhang, Jichun et al., "Electrochemical Array Microsystem with Integrated Potentiostat," 2005 IEEE, pp. 385-388.

Popovtzer, Rachela et al., "Electrochemical detection of biological reactions using a novel nano-bio-chip array," Feb. 28, 2006, pp. 664-672, 2006 Elsevier B.V., available online at www.sciencedirect.com.www.elsevier.com/locate/snb. DOI 10.1016/j.snb.2006.01.037.

Pavel, Steffan et al., "Electrochemical measurement System Based on Thick-Film Sensors," 2006 IEEE, pp. 204-207.

Nyholm, Leif, "Electrochemical techniques for lab-on-a-chip applications," The Royal Society of Chemistry 2005, pp. 599-605, The Analyst, www/rsc.org/analyst, DOI 10.1039/b415004j.

Ueno, Kosei et al., "Fabrication and electrochemical characterization of interdigitated nanoelectrode arrays," Dec. 9, 2004, pp. 161-165, www.sciencedirect.com, www.elsevier.com/locate/elecom. DOI 10.1016/j.elecom.2004.12.002.

"Post-CMOS Compatible Microfabrication of a Multi-Analyte Bioelectrochemical Sensor Array Microsystem", IEEE Sensors 2006, EXCP, Daegu, Korea—Oct. 22-25, 2006 (pp. 612-615).

* cited by examiner

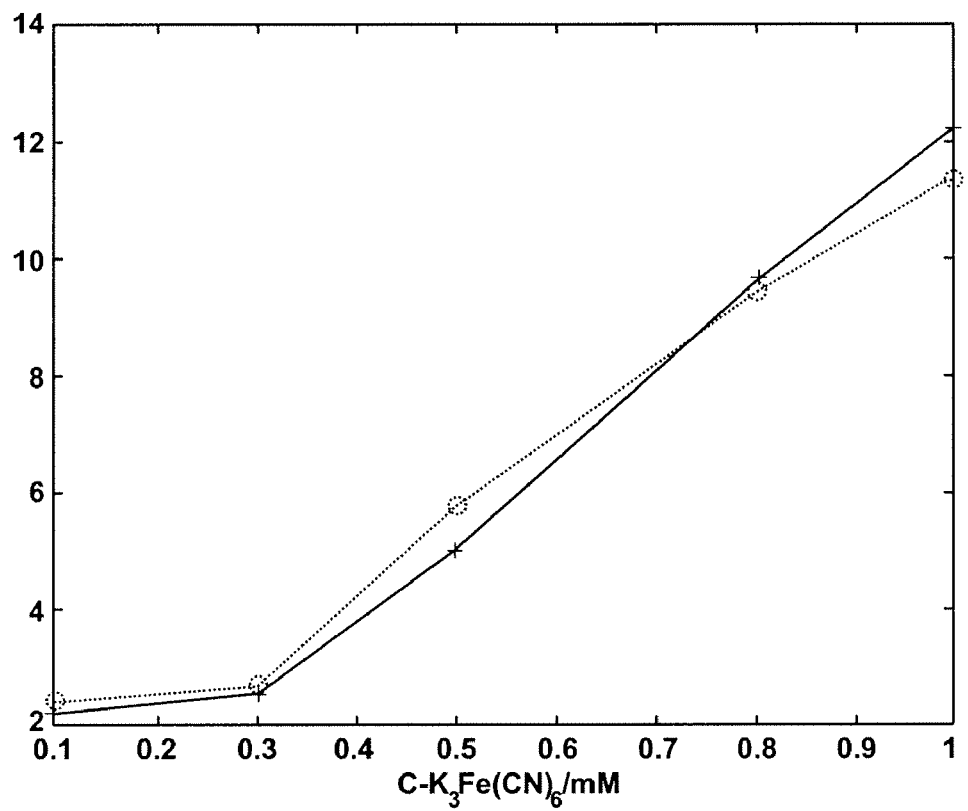
FIG. 27C
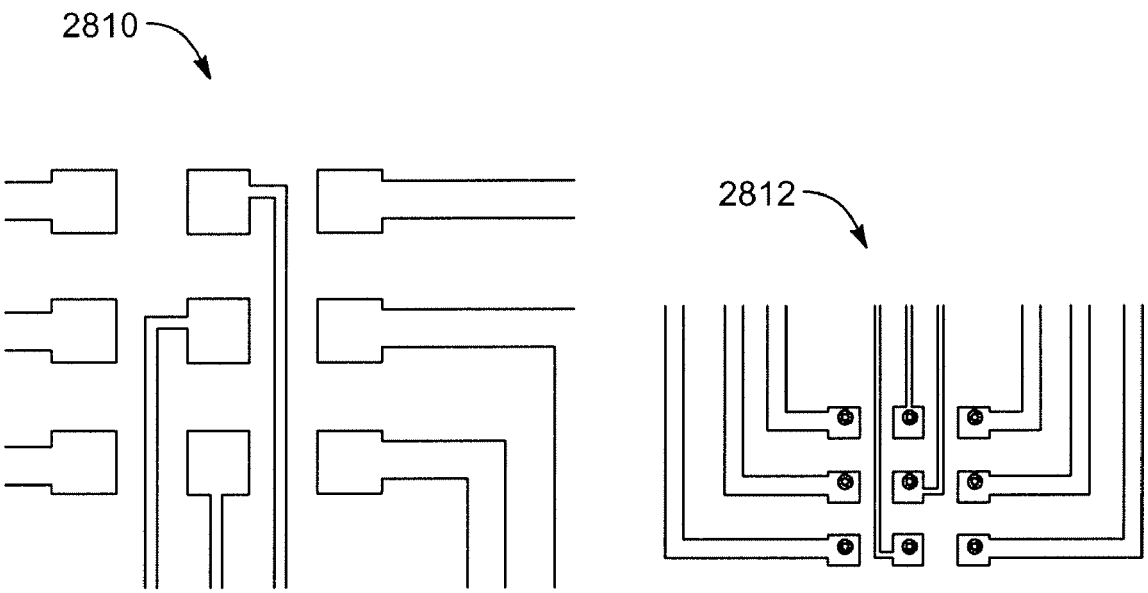
FIG. 28A  FIG. 28B

ELECTROCHEMICAL CHIP WITH MINIATURIZED SENSOR ARRAY

RELATED APPLICATION

This application claims the benefit under 35 U.S.C. §119(e) of U.S. Provisional Application No. 60/813,299, filed Jun. 12, 2006, which is hereby incorporated by reference herein in its entirety.

TECHNICAL FIELD

This disclosure relates generally to electrochemical analysis. More specifically, this disclosure relates to a portable, handheld electrochemical sensor device including a waveform generator integrated with potentiostat. This disclosure also relates to a microelectrode array useable with the handheld electrochemical sensor device.

BRIEF DESCRIPTION OF THE DRAWINGS

Non-limiting and non-exhaustive embodiments of the disclosure are described, including various embodiments of the disclosure with reference to the figures in which:

FIG. 27C schematically illustrates data combined from FIGS. 27A and 27B to further illustrate the consistency of responses from conventional electrochemical instruments and the systems and methods disclosed herein;

FIGS. 28A-28B are schematic diagrams of nine microelectrodes arranged in respective half arrays according to certain embodiments;

DETAILED DESCRIPTION OF PREFERRED EMBODIMENTS

Figure 1:
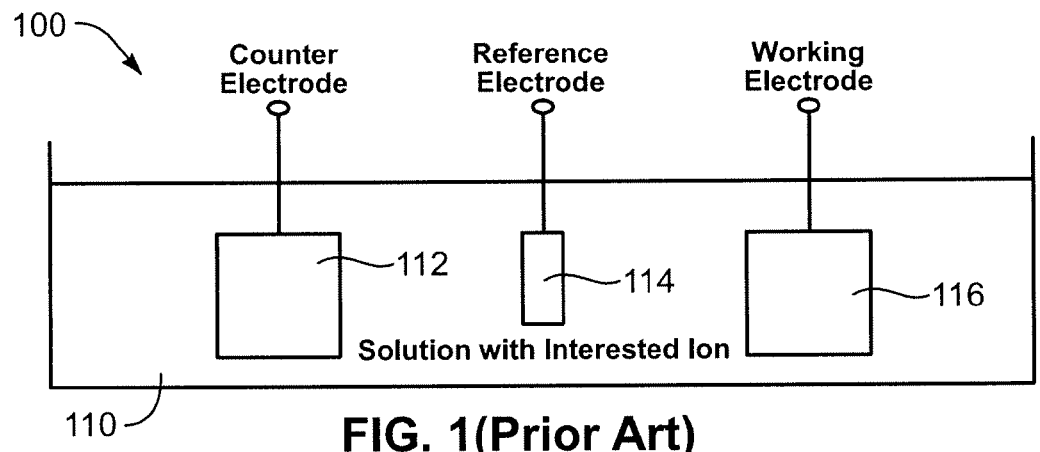
FIG. 1 is a block diagram of a conventional electrochemical cell setup.

Electrochemistry is especially useful in a variety of areas such as corrosion, coatings, electroplating and fuel cells. Through the knowledge of the electronic and electrical aspects of chemical reactions, and the investigation of the transfer of electrons, a current may be induced and measured in an electrolyte. The magnitude of this induced current offers information about the concentration of various ions in an aqueous solutions.

As discussed below, electrochemical cells are generally used to induce and measure the current in the electrolyte. At a negative electrode of the electrochemical cell, electrons are given off and "oxidation" takes place. At a positive electrode of the electrochemical cell, the excess electrons are collected and "reduction" occurs. This process of giving and taking of electrons creates an electric current (ion current). The ion current, which may be in a range of, for example, several Pico Amperes (pAs), may be used to determine ion concentrations. Thus, for example, water quality may be monitored and controlled by measuring the densities of ions such as Chloride, Sulfate, Magnesium, Calcium, Sodium, Bicarbonate, and Silica in rivers, lakes and other water bodies. Electrochemical cells may also be used, for example, in the biomedical field to analyze ion concentrations in bodily fluids. Of course, many other electrochemical analysis applications will occur to those skilled in the art.

In one embodiment, a handheld sensor device for measuring an ion concentration in a solution is provided. The solution is in an electrochemical cell that includes a counter electrode, a working electrode, and a reference electrode. The sensor device includes a control amplifier configured to provide a current through the counter electrode and the working electrode so as to maintain a predetermined voltage between the working electrode and the reference electrode. The sensor also includes a current amplifier configured to measure the current provided through the counter electrode and the working electrode.

In one embodiment, the sensor also includes a direct digital frequency synthesizer (DDFS) including a phase accumulator. The DDFS is configured to selectively generate a waveform specified by an electrochemical technique. In one such embodiment, the DDFS is configured, for example, to generate a waveform suitable for square wave voltammetry. Such a waveform may comprises a square wave of constant magnitude superimposed on a triangle wave. In one embodiment, the square wave has a frequency of approximately 15 Hz and the triangle wave has a frequency of approximately 0.1 Hz. However, in other embodiments, the square wave and the triangle waves have respective frequencies in a range between approximately 0.02 Hz and approximately 20 MHz. In other embodiments, the electrochemical technique may be cyclic voltammetry, linear sweep voltammetry, differential-pulse voltammetry, normal-pulse voltammetry, or other known electrochemical techniques.

In one embodiment, the current amplifier includes an electrically conductive guard configured to reduce a portion of the current measured by the current amplifier that is attributable to a leakage current through the reference electrode. In addition, or in another embodiment, the current amplifier may be configured to measure the current throughout an entire range comprising approximately 100 pA to approximately 2 mA.

In one embodiment, the handheld sensor also includes a lock-in amplifier including a phase sensitive detector. The lock-in amplifier is configured to reduce the measured current's noise.

In one embodiment, the handheld sensor is used with a microelectrode array formed on a glass substrate. In one such embodiment, the microelectrode array includes at least one microelectrode that is approximately 10 μm wide or less.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are neither shown nor described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

I. System Overview

FIG. 1 is a block diagram of a conventional electrochemical cell 100 used to measure an induced current. The magnitude of this induced current offers information about the concentration of various ions in an aqueous solution 110. The electrochemical cell 100 generally includes a counter electrode 112, a reference electrode 114, and a working electrode 116 immersed in the ionic solution 110.

Although not shown, electrochemical cells 100 generally include a potentiostat that controls the voltage difference between the working electrode 116 and the reference electrode 114 so as to maintain the voltage difference at a constant preset value. In practice, the potentiostat records potential differences between the working electrode 116 and the reference electrode 114 without polarizing the reference electrode 114. The potentiostat also compares the potential difference to the preset voltage and forces a current to go through the counter electrode 112 towards the working electrode 116 to counteract the voltage difference between the working electrode 116 and the reference electrode 114. According to the embodiments discussed herein, the potentiostat is configured to perform an accurate and stable generation and measurement of direct current (DC) voltages and currents.

Generally, there are several known electrochemical techniques such as cyclic voltammetry, linear sweep voltammetry, differential-pulse voltammetry, normal-pulse voltammetry and square wave voltammetry (SWV). SWV, for example, uses a square wave of constant amplitude superimposed on a staircase wave form. The current is measured at the end of each half-cycle. The current measured in the reverse half-cycle is subtracted from the current measured on the forward half-cycle. This current difference may be plotted as a function of the applied potential.

In certain example embodiments disclosed herein, an electrochemical chip is configured to use SWV. However, an artisan will understand from the disclosure herein that other electrochemical techniques may also be used. For example, in one embodiment, a user may selectively configure the electrochemical chip to use any particular electrochemical technique.

Figure 2:
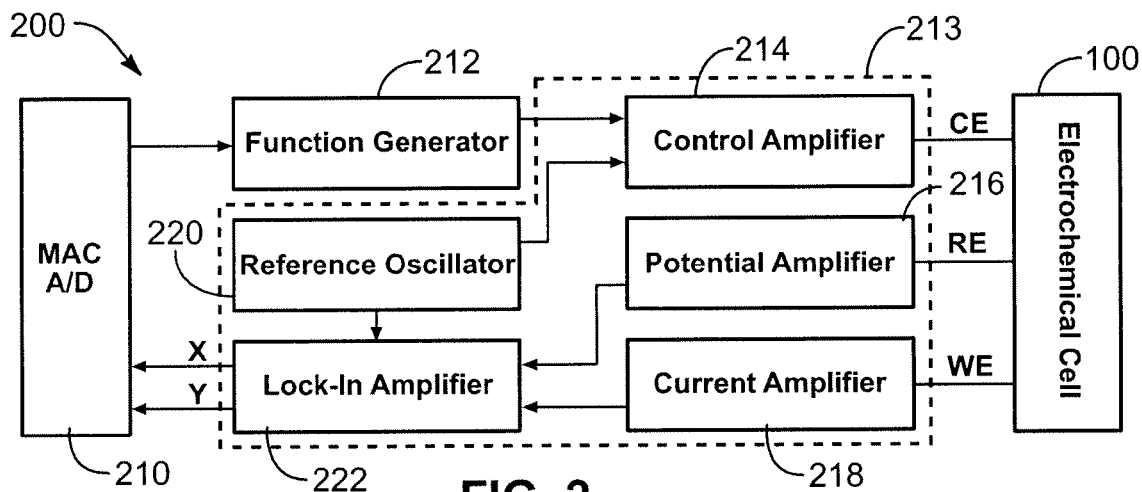
FIG. 2 is a block diagram of an example electrochemical chip according to one embodiment.

FIG. 2 is a block diagram of an example electrochemical sensor device 200 according to one embodiment. In one embodiment, the electrochemical sensor device 200 is a computerized hand-held test station on a printed circuit board. In another embodiment, the electrochemical sensor device 200 is integrated on a single chip. Thus, the electrochemical sensor device 200 may also be referred to herein as "electrochemical chip 200." The electrochemical chip 200 provides high accuracy and flexibility. The electrochemical chip 200 is also low cost as compared to conventional electrochemical systems.

The electrochemical chip 200 includes a measurement and control (MAC) unit 210 configured to manage data acquisition and potentiostat functionality. The MAC unit 210 may include, for example, a processor (e.g., an 8-bit Microcontroller Unit (MCU) or other processor) and an analog-to-digital (A/D) converter. The MAC unit 210 may also include an interface (e.g., RS-232, universal serial bus (USB), or other computer interface) configured to provide communication with a host computer (not shown) through which a user may define an electrochemical technique to be applied and monitor results through a graphical user interface (GUI). Thus, the electrochemical chip 200 may be configured to sample a potential-current wave and process the potential-current wave for display by a host computer.

The electrochemical chip 200 also includes a digital function generator 212 integrated with a potentiostat 213 in a single, portable sensor device. The potentiostat 213 includes a control amplifier 214, a potential amplifier 216, a current amplifier 218, a reference oscillator 220, and a lock-in amplifier 222. The digital function generator 212 is configured to generate (for this example) an SWV signal. The control amplifier 214 is electrically connected to the electrochemical cell 100 through the counter electrode 112 (CE). As discussed in detail below, the control amplifier 214 is also configured to integrate the functions of a signal amplifier, a power amplifier, and a low-pass filter. The potential amplifier 216 is electrically connected to the electrochemical cell 100 through the reference electrode 114 (RE) and includes a voltage follower with high input impedance.

The current amplifier 218 is electrically connected to the electrochemical cell 100 through the working electrode 114 (WE) and is configured to amplify ultra-low current. Generally, investigation in material science includes measuring ultra-low current in a range between approximately 100 pA and approximately 1 mA. The dynamic range of a good potentiostat spans up to 4 decades. The reference oscillator 220 may include a high accuracy, low frequency oscillator and may be derived from, for example, the MCU using programming and an on-chip timer.

The lock-in amplifier 222 is configured to separate a small, narrow band signal from interfering noise. As discussed below, the lock-in amplifier may include, for example, a narrow band pass filter to remove much of the unwanted noise while allowing the signal to be measured.

Various example embodiments of the electrochemical chip 200 and/or its various components are provided below. An artisan will recognize from the disclosure herein that the example embodiments may be combined in various ways and that the generalized interconnections between components illustrated in FIG. 2 may not apply to every specific example discussed herein.

II. Example Function Generator Embodiments

Figure 3:
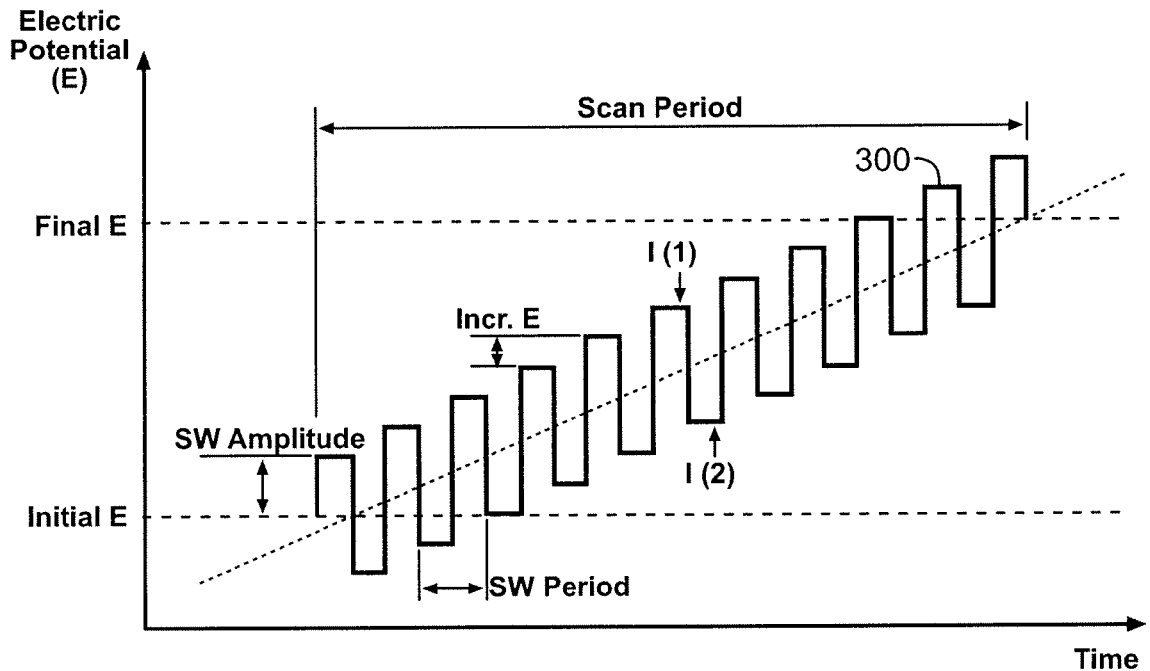
FIG. 3 schematically illustrates an example electric potential waveform suitable for a square wave (SW) voltammetry technique according to one embodiment.

As discussed above, the function generator 212 (according to the examples discussed herein) is configured to generate a SWV signal at the counter electrode 112. FIG. 3 schematically illustrates an example electric potential (E) waveform 300 suitable for a square wave (SW) voltammetry technique according to one embodiment. The waveform 300 provided to the counter electrode 112 comprises a square wave of constant amplitude superimposed on a stair case waveform. As discussed above, the current of the waveform is measure at the end of each half-cycle and the current measured in the reversed half cycle (see I(2) in FIG. 3) is subtracted from the current measured on the forward half-cycle (see I(1) in FIG. 3). This current difference may be displayed as a function of the applied potential.

The waveform 300 shown in FIG. 3 is defined by various parameters such as initial E, final E, incremental E, SW amplitude, SW frequency (1/period), and scan period. Table 1 below provides example values for the waveform 300 according to one embodiment. Note that in these examples, the waveform 300 may have a positive slope (rising staircase) or a negative slope (descending staircase).

TABLE 1

| Parameter | Example Approximate Value | Example Approximate Range | Units |
|---|---|---|---|
| SW Amplitude | 0.025 | 0.0006 to 2.5 | Volts |
| SW Frequency | 15.0015 | 0.02 to 20 × 10$^6$ | Hertz |
| Incremental E | 0.004 | 0.0006 to 2.5 | Volts |
| Initial E | 0.5 | −5 to +5 | Volts |
| Final E | −0.1 | −5 to +5 | Volts |

From the example approximate values shown in Table 1, the scan period may be calculated as: Scan Period=(Init E−Final E)/Incr. E*(1/SW Freq)=9.999 seconds.

The waveform 300 shown in FIG. 3 (or similar waveforms) may be generated in various ways, including using both analog and digital circuitry. For example, the waveform 300 may be generated by an RC and Schmitt circuit, a summing amplifier, an RC and Schmitt circuit with a constant current source, or a direct digital frequency synthesizer. Details for such example embodiments, along with some discussion of corresponding advantages and disadvantages, are provided below.

A. RC and Schmitt Circuit

Figure 4:
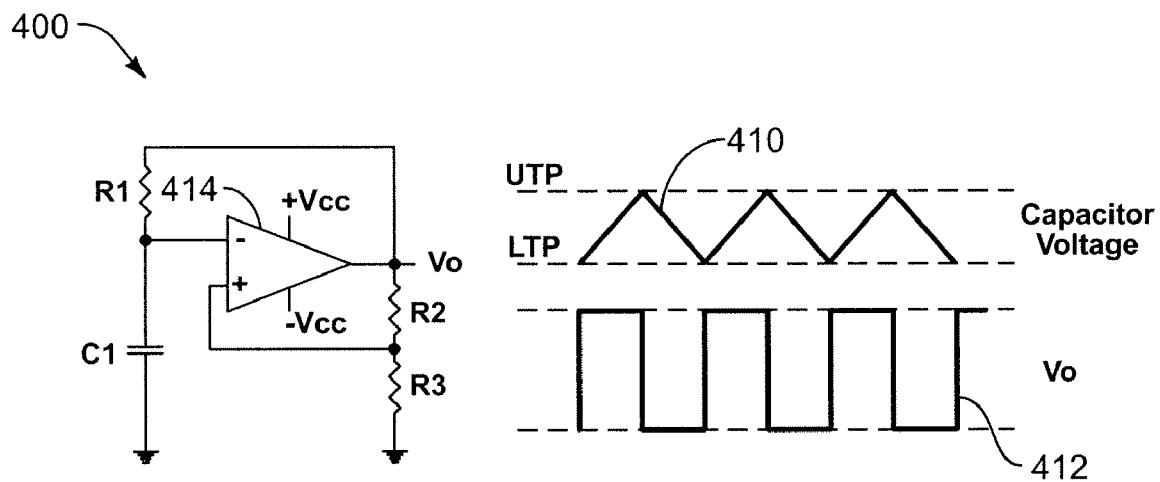
FIG. 4 is a schematic diagram of an RC and Schmitt circuit and resulting waveforms according to one embodiment.

The SW function generator 212 may be constructed by adding a resistor and a capacitor to an inverting Schmitt trigger circuit. For example, FIG. 4 is a schematic diagram of an RC and Schmitt circuit 400 and resulting waveforms 410, 412 according to one embodiment. The Schmitt trigger portion of the circuit 400 includes an operational amplifier 414 together with two resistors R2, R3. However, in this embodiment, a capacitor C1 controls the voltage at the Schmitt input and a resistor R1 charges and discharges the capacitor C1 from the Schmitt output Vo.

The RC and Schmitt circuit 400 shown in FIG. 4 may not provide sufficient linearity for certain applications. Thus, it may be necessary to set an upper tuning point (UTP) and a lower tuning point (LTP) that are much smaller than the operational amplifier's output levels and to keep the voltage drop across the resistor R1 approximately constant. Thus, the capacitor charging current is maintained at a substantially constant value.

Figure 5:
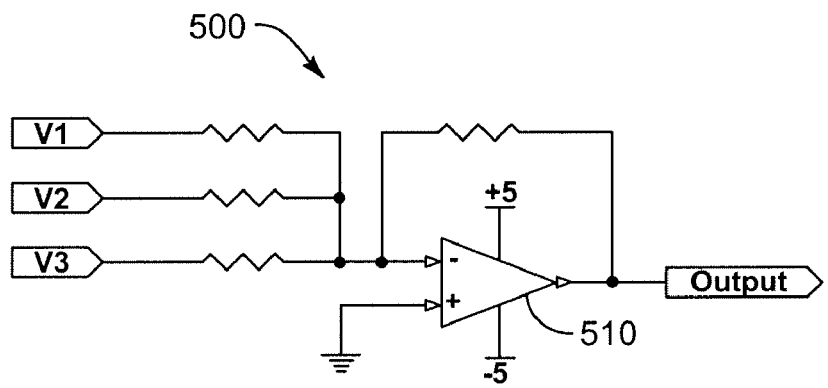
FIG. 5 is a schematic diagram of a summing amplifier circuit for generating a waveform according to one embodiment.

In one embodiment, the SW function generator 212 also includes a summing amplifier circuit configured to combine, for example, a square wave and a triangle wave to produce a final waveform such as the waveform 300 shown in FIG. 3. For example, FIG. 5 is a schematic diagram of a summing amplifier circuit 500 for generating a waveform according to one embodiment. The summing amplifier circuit 500 receives two or more inputs (V1, V2, V3) and provides an output voltage that is proportional to the negative of the algebraic sum of its input voltages as represented by the following equation:

$$V_{out} = -\left(\frac{V_1}{R} + \frac{V_2}{R} + \frac{V_3}{R}\right)R.$$

If all resistors shown in FIG. 5 have the same value, then $V_{out}=-(V_1+V_2+V_3)$.

An advantage of the summing amplifier circuit 500 is that three operational amplifiers (e.g., one used to produce a square wave, one used to produce a triangle wave, and an operational amplifier 510 used for the summing amplifier circuit 500) and several resistors and capacitors are enough to provide a desired waveform. A disadvantage, however, is poor accuracy and linearity. When frequency is low, linearity begins to deteriorate. For example, when the frequency is as low as approximately 100 Hz, the linearity may not be acceptable for certain applications.

B. RC and Schmitt Circuit with Constant Current Source

Figure 6:
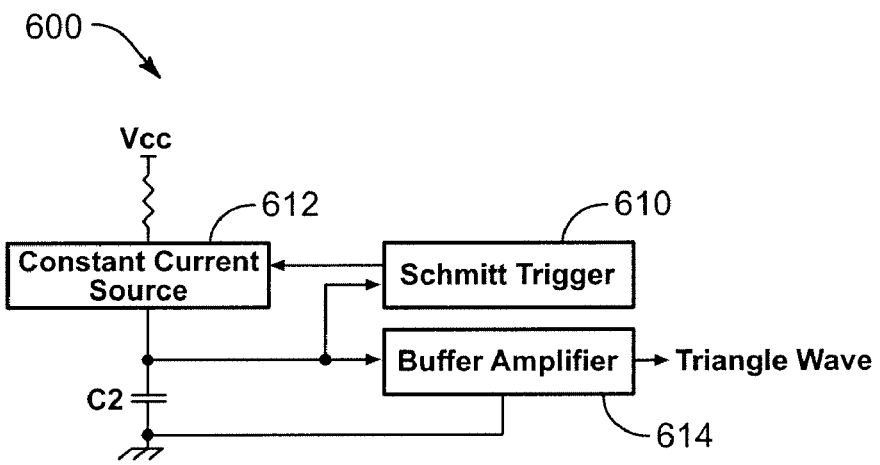
FIG. 6 is a partial schematic diagram and partial block diagram of an RC and Schmitt circuit with a constant current source according to one embodiment.

In another embodiment, the function generator 212 also includes a constant current source to improve the linearity of a capacitor voltage. For example, FIG. 6 is a partial schematic diagram and partial block diagram of an RC and Schmitt circuit 600 with a constant current source according to one embodiment. The circuit 600 includes a Schmitt trigger 610 (e.g., the operational amplifier 414 and resistors R2, R3 shown in FIG. 4) electrically coupled to a constant current source 612, a capacitor C2, and a buffer amplifier 614. Although not shown, the output of the Schmitt trigger 610 may also be electrically coupled to an additional buffer amplifier so as to provide a square wave. With the help of the constant current source 612, the circuit 600 provides a highly linear triangle wave output having a highly stable center frequency at a wide range of operating voltages.

Figure 7:
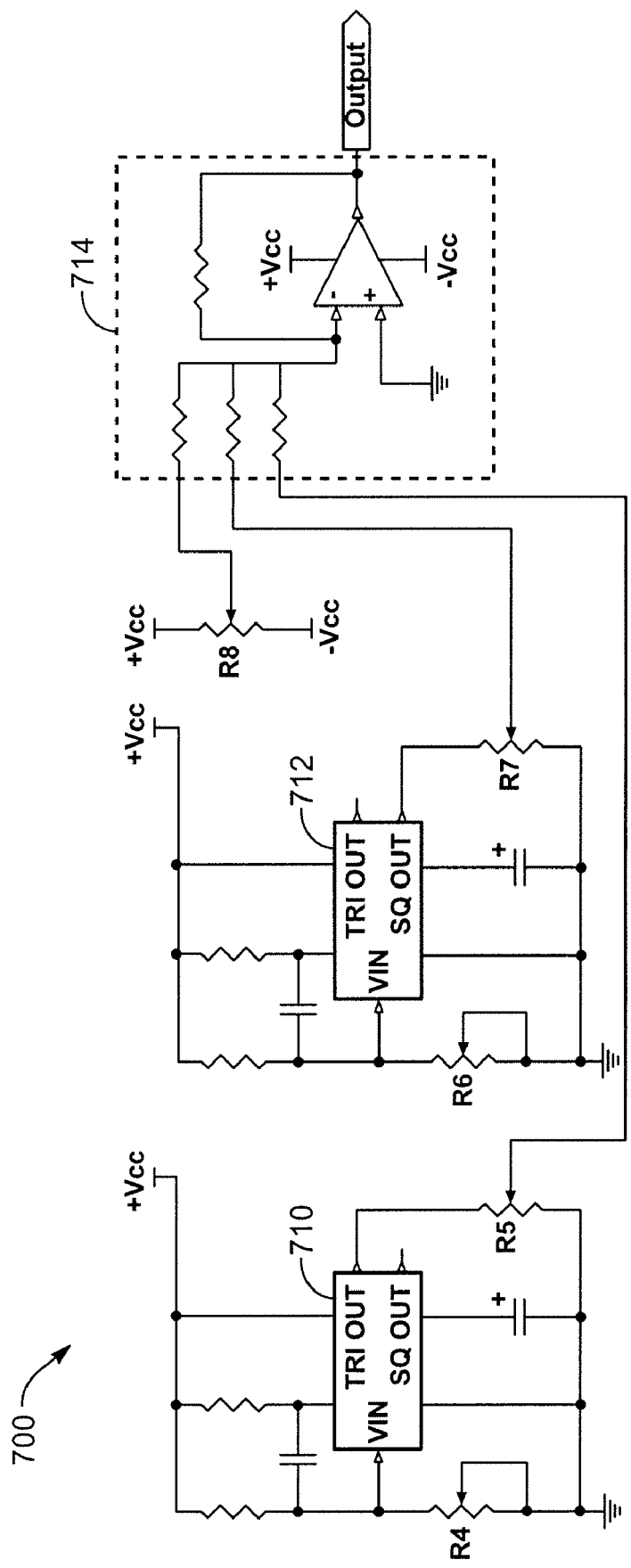
FIG. 7 is a schematic diagram of a SW function generator circuit that includes RC and Schmitt circuits with constant current sources and a summing amplifier circuit according to one embodiment.

FIG. 7 is a schematic diagram of a SW function generator circuit 700 that includes RC and Schmitt circuits 710, 712 with constant current sources, and a summing amplifier circuit 714 according to one embodiment. The circuit 700 provides simplicity and is low cost. The RC and Schmitt circuits 710, 712 with constant current sources may include, for example, the circuit 600 shown in FIG. 6. In one embodiment, the RC and Schmitt circuits 710, 712 with constant current sources each comprise an NE566 function generator available from Philips Semiconductor Linear Products, which is a voltage-controlled oscillator of exceptional linearity with buffered square wave and triangle wave outputs.

The frequency of oscillation of the NE566 function generator is determined by external resistors and capacitors and a voltage applied to a control terminal (VIN). A resistor R4 may be adjusted to change the frequency of the triangle wave, a resistor R5 may be adjusted to change the slope of the triangle wave, a resistor R6 may be adjusted to change the frequency of the square wave, a resistor R7 may be adjusted to change the amplitude of the square wave, and a resistor R8 may be adjusted to change the DC potential of whole wave (e.g., at the output of the summing amplifier 714).

Using an internal constant current source, the NE566 provides acceptable linearity within a working triangle wave frequencies ranging between approximately 3 Hz and approximately 1 MHz. When the frequency of the triangle wave is as low as approximately 0.5 Hz, the linearity may not be acceptable for certain applications. In one embodiment, for example, the SWV specification is approximately 0.1 Hz. In such an embodiment, the frequency is beyond the ability of the NE566's internal constant current source circuit. However, the circuit 700 using the NE566 with the constant current source circuit may be utilized in some applications where, for example, electrochemical reactions are finished within a short time period.

Figure 8:
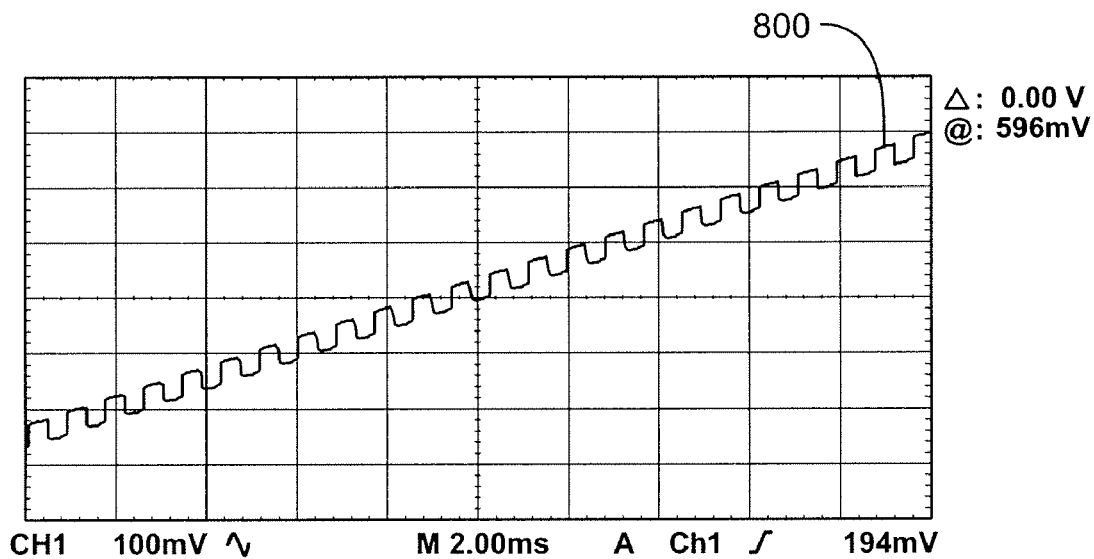
FIG. 8 schematically illustrates an example waveform generated by the SW function generator circuit shown in FIG. 7 according to one embodiment.

FIG. 8 schematically illustrates an example waveform 800 generated by the SW function generator circuit 700 shown in FIG. 7 according to one embodiment. In this example, the waveform 800 is synthesized by combining a triangle wave having a frequency of approximately 10 Hz and a square wave having a frequency of approximately 1000 Hz.

C. Direct Digital Frequency Synthesizer (DDFS)

In another embodiment, the function generator 212 includes a direct digital frequency synthesizer (DDFS) to generate a desired waveform. Generally, the DDFS has been used in the telecommunication field for its high frequency resolution and wide frequency bandwidth. As disclosed herein, the DDFS is used to provide flexibility when generating a user-defined waveform of ultra-low frequency.

Figure 9:
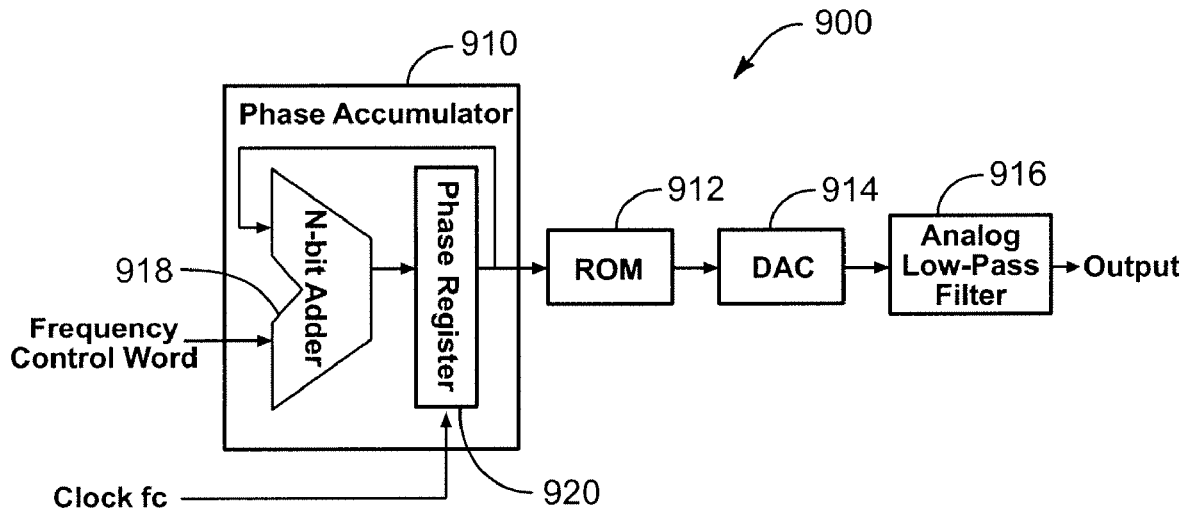
FIG. 9 is a block diagram of a direct digital frequency synthesizer (DDFS) configured to generate a user-defined ultra-low frequency waveform according to one embodiment.

FIG. 9 is a block diagram of a DDFS 900 configured to generate a user-defined ultra-low frequency waveform according to one embodiment. The DDFS 900 includes a phase accumulator 910, a read only memory (ROM) 912, a digital-to-analog converter (DAC) 914, and an analog low-pass filter 916. The phase accumulator 910 includes a binary N-bit full-adder 918 and an N-bit phase register 920. The N-bit full-adder 918 includes two inputs that are the inputs to the phase accumulator 910. The phase register 920 provides the output of the phase accumulator 910.

The output of the phase accumulator 910 is fed back to one of the adder's inputs. A second adder input, frequency control word (FCW), is added to the phase accumulator on every clock cycle. A clock with a frequency fc is the synthesizer's time reference. The full-adder 918 causes the contents of the phase register 920 to increase by the value FCW at the end of each clock cycle.

The phase accumulator's output overflows to zero periodically. The output of phase accumulator 910 is a sampled saw-tooth wave with a repetition frequency $$f_{out} = f_c \times \frac{FCW}{2^N},$$

and an output frequency resolution $$\Delta f = \frac{f_c}{2^N}.$$

From these equations, it is clear that $f_c$, FCW, and the length of phase accumulator 910 control the output frequency and the frequency resolution. For example, if $f_c$ is 5 kHz, FCW is 1 Hz, and the phase accumulator 910 has a length of 16-bits, then the output frequency is lower than 0.1 Hz and will satisfy the SWV specification. If the FCW changes, the amount of accumulated phase will change irregularly. This may be considered as a phase jitter in the output signal. Thus, in one embodiment, the FCW remains unchanged.

The output of the phase accumulator 910 forms the address of the ROM based look-up table (LUT). The size of the ROM 912 grows exponentially with the width of the phase accumulator 910. However, in certain embodiments it is desirable to use a wide phase accumulator 910 to achieve fine frequency resolution. This controversy may be neglected in some embodiments because a 16-bit phase accumulator is sufficient for the 0.1 Hz output frequency. The output signal of the DAC 914 followed by the anti-alias low-pass filter 916 is a pure signal (e.g., free of harmonic distortion). In such embodiments, the Nyquist condition: $f_c > 2 \times f_{out}$ is satisfied.

1. Example DDFS Circuit Implementation

Figure 10:
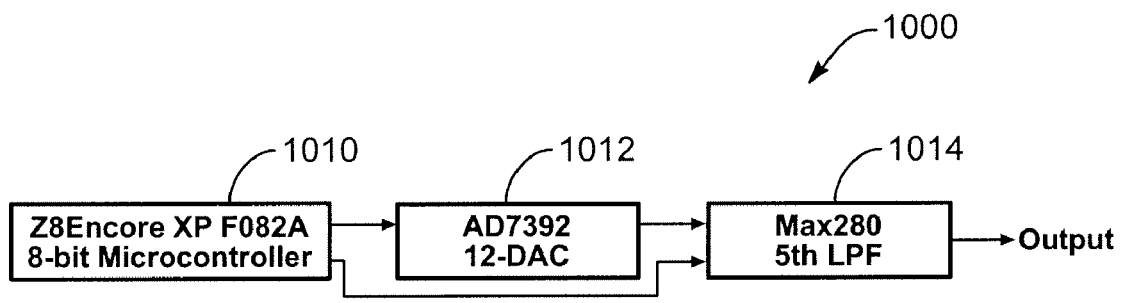
FIG. 10 is a block diagram of an example DDFS circuit according to one embodiment.

FIG. 10 is a block diagram of an example DDFS circuit 1000 according to one embodiment. The example DDFS circuit 1000 includes an 8-bit microcontroller 1010, a DAC 1212, and a low-pass filter (LPF) 1014. In this example embodiment, the microcontroller 1010 includes a Z8 Encore XP F082A microprocessor available from ZiLOG, Inc. of San Jose, Calif. The F08XA series devices support 8 KB of flash program memory and 1 KB register RAM. The flash in-circuit programming capability allows for faster development and program changes in the field. The F08XA devices include rich peripherals that make them very suitable for the low frequency DDFS embodiments disclosed herein.

The F08XA devices provide up to 20 MHz system clock. In conventional DDFS designs, there is generally a separate field-programmable gate array (FPGA)/MCU to finish the DDFS due to the consideration of frequency accuracy. In this example embodiment, however, the target frequency is very low and processing speed is around 10 MIPS. Thus, no extra chips (FPGAs/MCUs) are needed. The F08XA devices also provide: an 8 KB flash memory with in-circuit programming capability and 1 KB register RAM; 25 general purpose input/output (IO) pins (28 pin package) wherein each pin is individually programmable; an internal precision oscillator, which requires no external components; a full-duplex universal asynchronous receiver/transmitter (UART) capable of handling asynchronous data transfers; two enhanced 16-bit timers that may be used for timing/counting events; an on-chip debugger (OCD) that provides a rich set of debugging capabilities such as reading and writing register, programming flash memory, and setting breakpoints; a single pin interface that provides communication to the OCD; an 8-channel, 10-bit DAC; up to 20 vectored interrupts that include eight internal peripheral interrupts and twelve general-purpose IO (GPIO) pin interrupt sources and have three levels of programmable interrupt priority; and power-on reset functionality.

In this example embodiment, the DAC 1012 includes an AD7392 analog-to-digital converter (ADC) available from Analog Devices, Inc. of Norwood, Mass. The AD7392 ADC is a general purpose 12-bit, voltage-switched, laser-trimmed parallel ADC. The voltage switched R-2R DAC generates an output voltage dependent on the external reference voltage connected to the REF pin according to following equation:

$$V_{out} = V_{REF} \times \frac{D}{2^N}.$$

In one embodiment, $V_{REF}$ is approximately 2.5V and N=12, so that:

$$V_{out} = V_{REF} \times \frac{D}{4096}.$$

The output of the DAC 1012 may include some unwanted high frequency noise. The LPF 1014 is configured to reduce or remove this noise. In this example embodiment, the LPF 1014 includes a MAX280 $5^{th}$ order LPF available from Maxim Integrated Products, Inc. of Sunnyvale, Calif. The LPF 1014 uses an external resistor and capacitor to isolate the MAX280 integrated circuit from the DC signal path to provide excellent DC accuracy. The resistor and capacitor, along with an on-chip $4^{th}$ order switch capacitor filter, forms a $5^{th}$-order LPF. The cutoff frequency is set by an internal clock that may be externally driven. The clock to cutoff frequency ratio in one embodiment is 100:1.

The desired cutoff frequency and the resistor and capacitor should be chosen such that:

$$\frac{f_{cut}}{1.62} = \frac{1}{2\pi RC}$$

$f_{cut}$: filter cutoff frequency (−3 dB point).

If $f_{cut}$=30 Hz, R=15 k, C=560 pF, filter gain is given by:

$f_{in}$=0.5$f_{cut}$ $G_{filter}$=−0.02 dB;

$f_{in}$=$f_{cut}$ $G_{filter}$=−3 dB;

$f_{in}$=2$f_{cut}$ $G_{filter}$=−30 dB;

$f_{in}$=4$f_{cut}$ $G_{filter}$=−60 dB.

Figure 11:
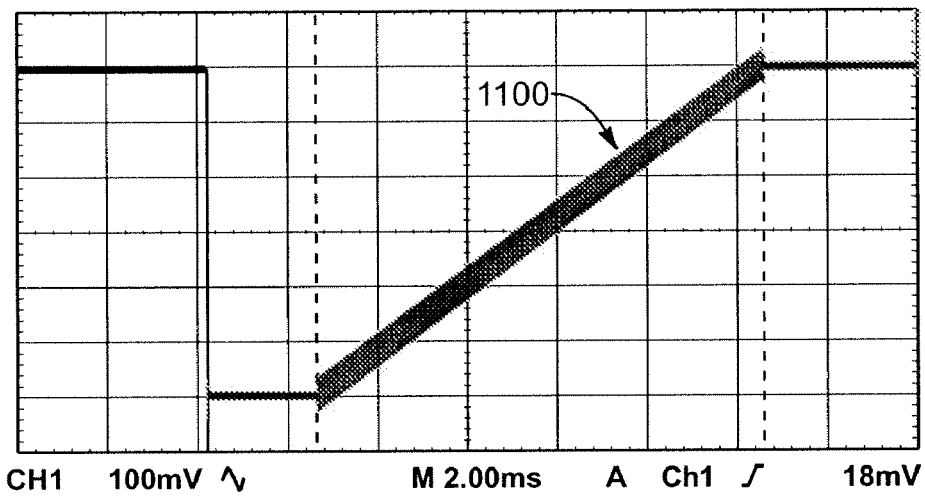
FIG. 11 schematically illustrates an example waveform generated by the example DDFS circuit shown in FIG. 10 according to one embodiment.
Figure 12:
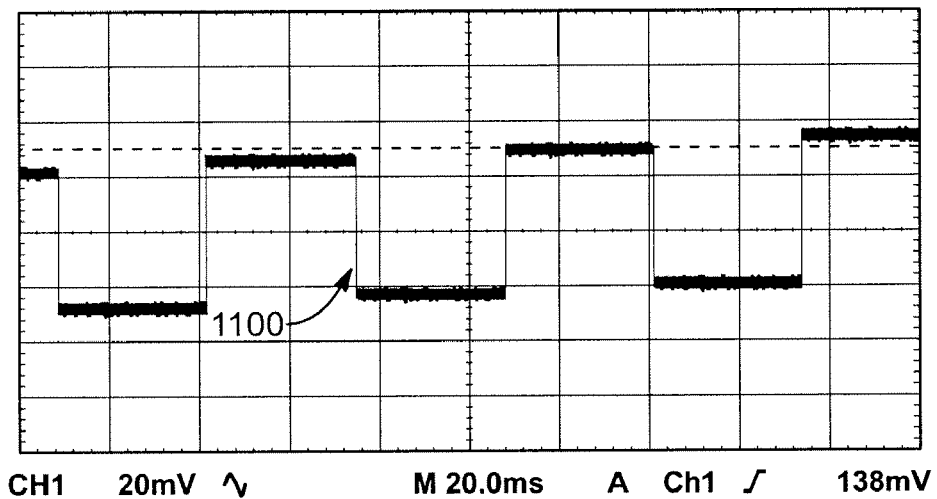
FIGS. 12-13 schematically illustrate enlarged versions of the waveform shown in FIG. 11 to provide additional details.
Figure 13:
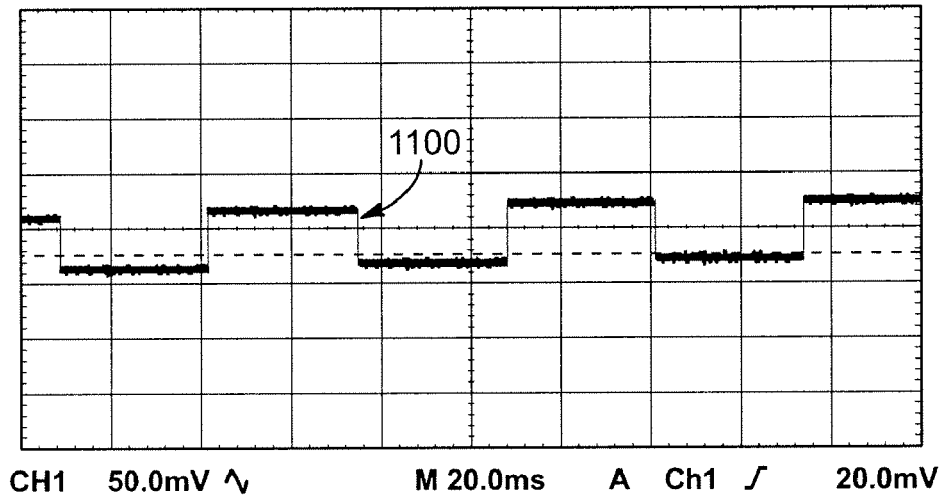

FIG. 11 schematically illustrates an example waveform 1100 generated by the example DDFS circuit 1000 shown in FIG. 10 according to one embodiment. In this example, the DDFS circuit 1000 synthesizes the waveform 1100 as the combination of a triangle wave having a frequency of approximately 0.1 Hz and a square wave having a frequency of approximately 15 Hz. FIGS. 12-13 schematically illustrate enlarged versions of the waveform 1100 shown in FIG. 11 to provide additional details.

Figure 14:
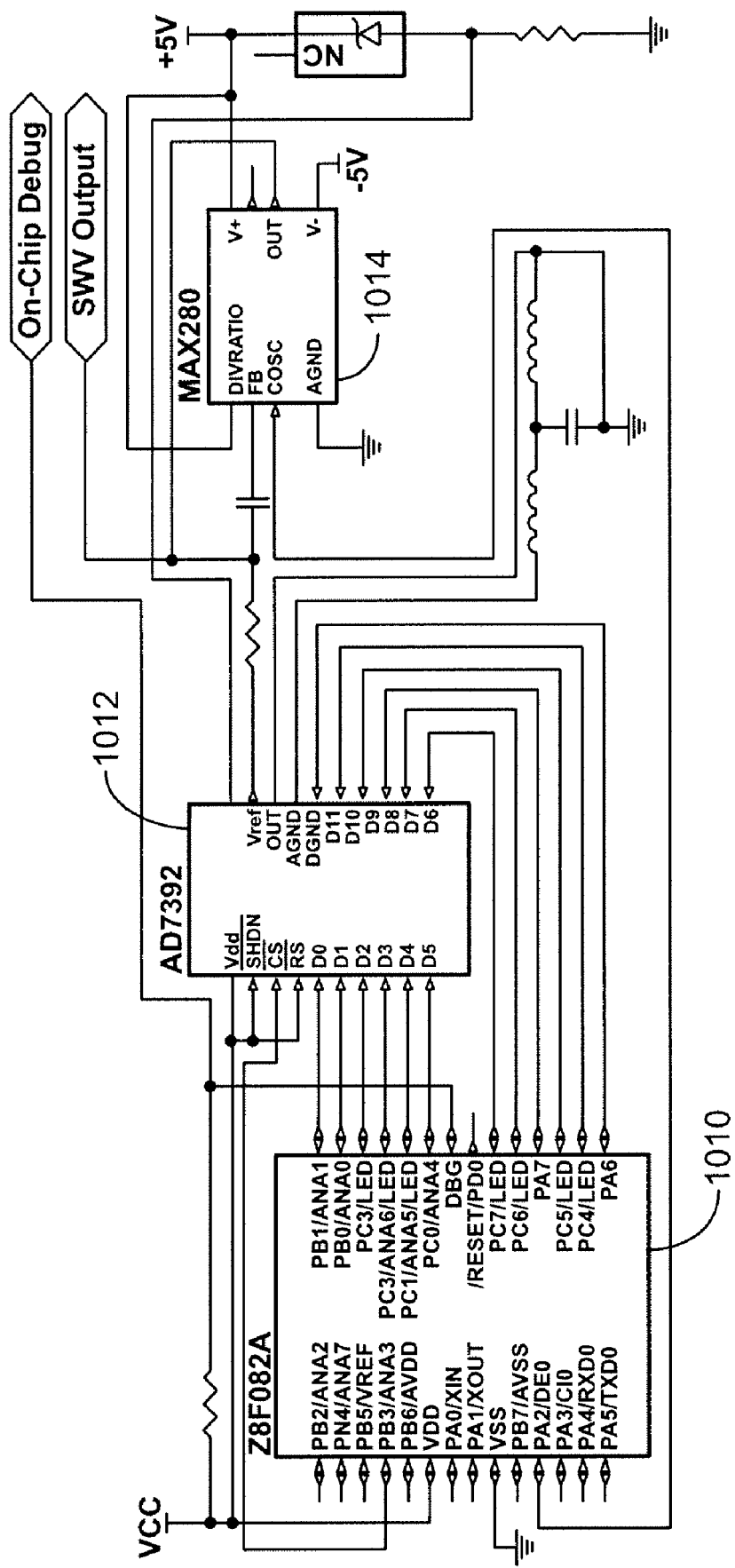
FIG. 14 is a schematic diagram of the example DDFS circuit shown in FIG. 10 according to one embodiment.

FIG. 14 is a schematic diagram of the example DDFS circuit 1000 shown in FIG. 10 according to one embodiment. FIG. 14 shows detailed interconnections between the example Z8 F082A microprocessor 1010, the AD7392 ADC 1012, and the MAX280 LPF 1014 discussed above.

III. Example Control Amplifier Embodiments

The control amplifier 214 (see FIG. 2) is configured to maintain a potential between the working electrode 116 and the reference electrode 114 of the of the electrochemical cell 100 (see FIG. 1) at a preset value. The control amplifier 214 determines whether current is necessary to flow between the working electrode 116 and the counter electrode 112 so as to keep the preset potential, as long as the cell voltage and current do not exceed the compliance limits of the potentiostat. If a current passes through the reference electrode 114, the reference electrode 114 will be polarized such that the potential of the reference electrode 114 varies with the current. Thus, to maintain a stable potential between the reference electrode 114 and the working electrode 116, no current (with the exception of possible leakage current discussed below) is allowed to pass through the reference electrode 114. According to one embodiment, the control amplifier 214 therefore has a very high input impedance in a range between approximately $10^{12}$ Ohms and approximately $10^{15}$ Ohms.

The control amplifier 214 is configured to perform at least the following three tasks: (1) measure and maintain the potential between the reference electrode 114 and the working electrode 116 at a preset value; (2) offer enough current flow from the counter electrode 112 toward the working electrode 116 in order to counteract the difference between the preset potential value and an existing working electrode potential; and (3) offer high input impedance at the reference electrode 114, preventing it from polarizing.

Figure 15:
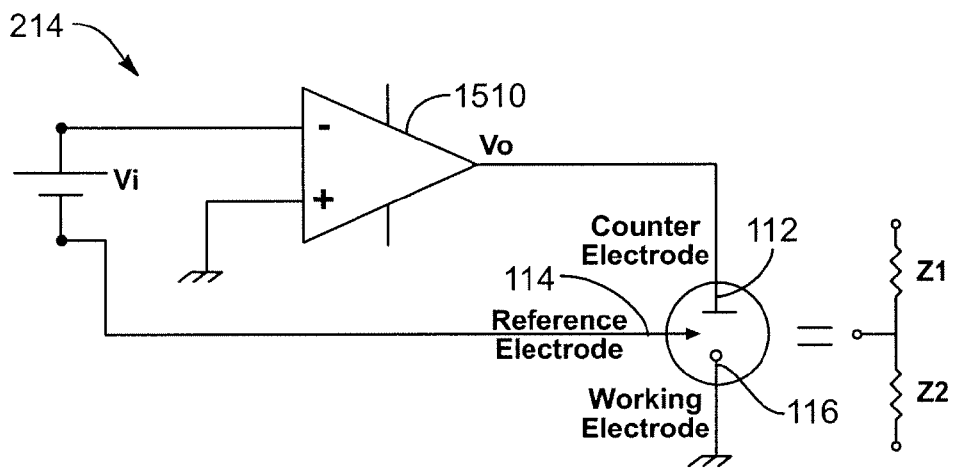
FIG. 15 is a block diagram of a control amplifier according to one embodiment.

FIG. 15 is a block diagram of a control amplifier 214 according to one embodiment. The control amplifier 214 includes an operational amplifier 1510 electrically coupled to the counter electrode 112. FIG. 15 illustrates the impedance between the electrodes 112, 114, 116 as Z1 and Z2. Because the input impedance of the operational amplifier 1510 is high, substantially no current will flow from the inverting input to the noninverting input. Thus, the potential of the inverting input is substantially equal to the noninverting input, which is grounded.

A predetermined reference voltage, $V_{RE}$=−$V_i$ (with reference to the working electrode 116), is a fixed value and does not change with the fluctuation of Z1 or Z2. The output voltage $V_o$ (into the counter electrode 112) is also a fixed value and is give by (with reference the working electrode 116):

$$V_o = -V_i \frac{Z_1 + Z_2}{Z_2}.$$

Thus, the potential between the reference electrode 114 and the working electrode 116 is fixed and equal to a predetermined input voltage $V_i$.

The basic control amplifier circuit shown in FIG. 15 lacks an additional input channel for a control signal. Further, the reference electrode 114 must supply a significant current to the summing point, which may cause the reference electrode 114 to polarize. Further, the power that is available at the cell 100 may only include power that is available from the output of the operational amplifier 1510.

Figure 16:
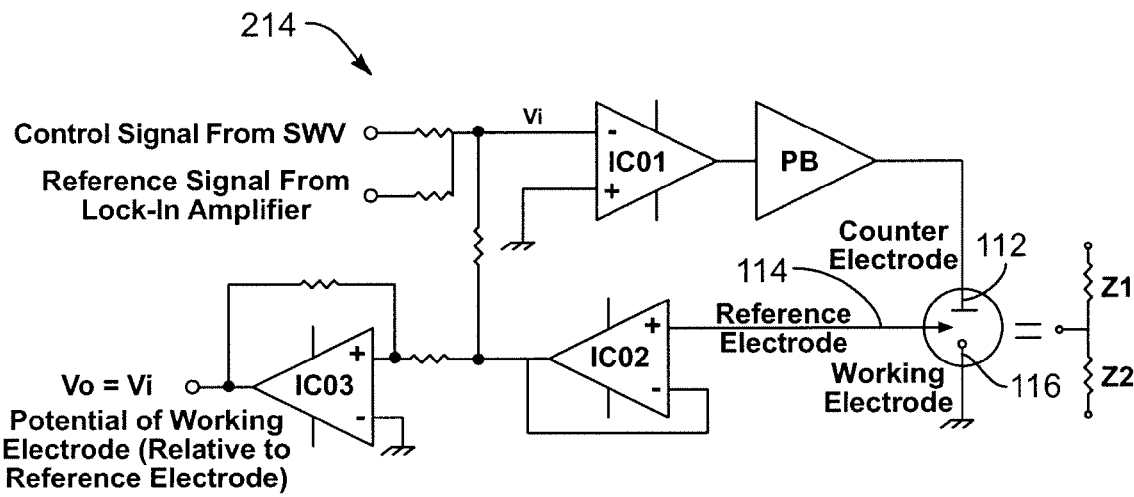
FIG. 16 is a block diagram of a control amplifier according to another embodiment.

FIG. 16 is a block diagram of a control amplifier 214 according to another embodiment. The control amplifier 214 shown in FIG. 16 includes four operational amplifiers IC01, IC02, IC03, PB. The operational amplifier IC01 is configured as a pre-amplifier and the operational amplifier PB is configured as a power booster. Increased power is achieved by inserting power boosting amplifier PB in the output loop. The power boosting amplifier (PB) is configured as unit gain current amplifier capable of delivering higher currents or higher voltages than the operational amplifier IC01. The power boosting amplifier (PB) follows the pre-amplifier (IC01) to handle a large working current and provides DC-DC coupling. The output potential is equal to the DC potential of the pre-amplifier (IC01).

The operational amplifier IC02 is configured as a voltage follower inserted into the feedback loop. The voltage follower (IC02) works as an impedance transformer to obtain high input impedance. This prevents the reference electrode 114 from polarizing. The voltage follower (IC02) also provides summing current without influencing the potential of the reference electrode 114.

The operational amplifier IC03 is configured as an inverting voltage converter with unit gain. The output voltage the inverting voltage converter (IC03) may be measured and recorded as the potential value of the working electrode 116.

A. Example Control Amplifier Circuit Implementation

Figure 17:
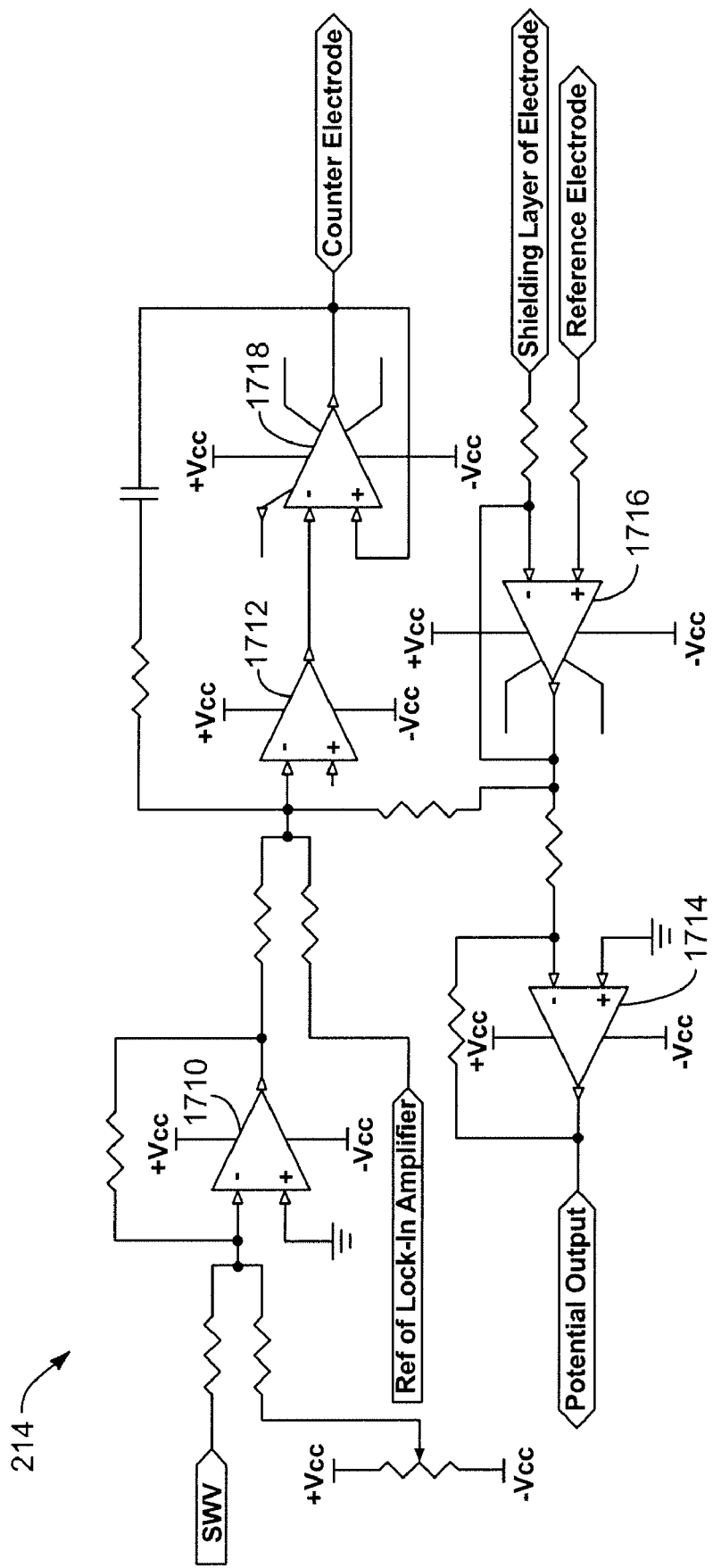
FIG. 17 is a schematic diagram of an example control amplifier circuit according to one embodiment.

FIG. 17 is a schematic diagram of an example control amplifier circuit 214 according to one embodiment. The control amplifier 214 includes operational amplifiers 1710, 1712, 1714, 1716, 1718. In one embodiment, the operational amplifier 1716 includes an ultra-low bias current DIFET high performance operational amplifier available from Burr-Brown Corp. of Tucson, Ariz. The fabrication of the DIFET 1716 may eliminate isolation-junction leakage current. The DIFET's input impedance of common-mode reaches approximately $10^{15}$ Ohms according to one embodiment. In one embodiment, the operational amplifier 1718 includes an high voltage, high current operational amplifier, also available from Burr-Brown Corp.

Ultra-low input bias current operational amplifiers may require precautions to achieve best performance. Leakage current on the surface of a circuit board, for example, may exceed the input bias current of the amplifier. To minimize surface leakage, a guard trace should completely surround the input terminals and other circuitry connecting to the inputs of the operational amplifiers. In this example embodiment, two pins next to the input pins have no internal connection. This allows an optimized circuit board layout with guarding. The shielding layer of a probe cable of the reference electrode 114 may also need guarding.

The operational amplifier 1710 provides DC offset of SWV. The DAC AD7392 discussed above is powered by a positive voltage source, but according to the requirement of SWV, the sweep wave ranges from approximately −0.1V to approximately 0.6V. Thus, the operational amplifier 1710 according to one embodiment is used to draw DC potential below a zero value. The operational amplifier 1712 is configured as a summing operational amplifier that sums the SWV, the reference signal from the lock-in amplifier 222, and feedback signal together. The operational amplifier 1714 is configured as a 1:−1 voltage converter. The operational amplifier 1714 also provides voltage gain needed for the ADC circuit discussed above.

IV. Example Current Amplifier Embodiments

As discussed above, the current amplifier 218 (see FIG. 2) is configured to transform the ion solution induced current into a voltage value, which is more convenient to measure. The current amplifier 218 measures the induced current at the end of each half-cycle. The current measured in the reversed half cycle is subtracted from the current measured in the forward half-cycle. This current difference is displayed according to one embodiment as a function of the applied potential.

In one embodiment, the maximum current value produced by SWV is approximately 2 mA. The actual induced current depends on the electrical activity of the ion solution 110. The usable span of current between full range and the lowest detectable current in the same range is called the potentiostat's dynamic. In one embodiment, the dynamic of the potentiostat spans four decades. For example, in one embodiment, the dynamic ranges from approximately 100 pA to approximately 2 mA.

Because the input impedance of the reference electrode 114 is very high, the current flow through the counter electrode 112 is almost the same as the current flow through the working electrode 116. As discussed below, the difference among various current measuring methods depends on the different placement of a range resistor Rr.

A. Basic Measuring Circuit

Figure 18:
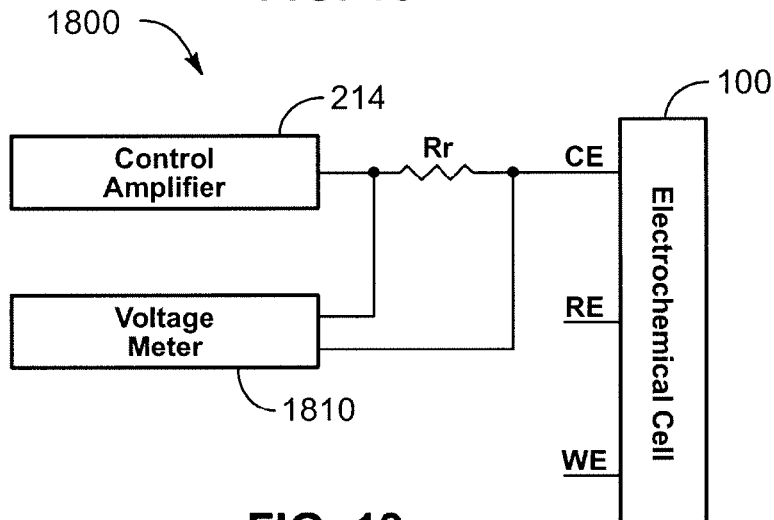
FIG. 18 is a block diagram of a basic measuring circuit according to one embodiment.

FIG. 18 is a block diagram of a basic measuring circuit 1800 according to one embodiment. In order to plot the current difference verses applied potential, the current flow through the counter electrode 112 and the working electrode 116 is measured. As shown in FIG. 18, one basic circuit for measuring the current includes a range resistor Rr in series with the counter electrode 112, across which a voltage develops proportional to the current passing through the range resistor Rr. In this example embodiment, the working electrode 116 remains on true ground and the circuit is not sensitive to noise. However, in this embodiment, a voltage meter 1810 requires a floating input, which is difficult to implement.

B. Floating Power Supply Circuit

Figure 19:
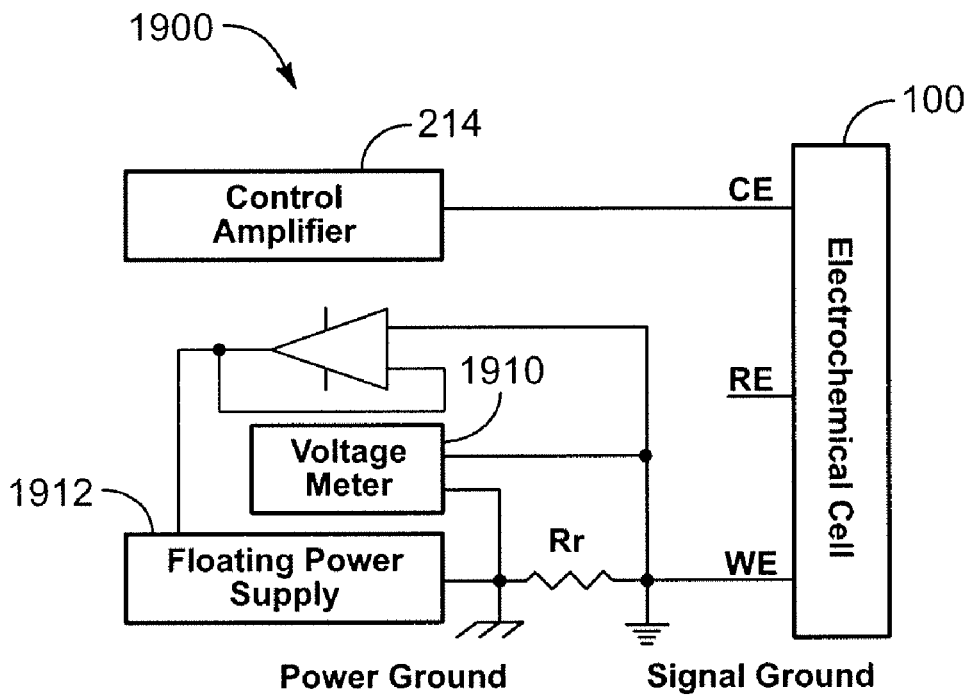
FIG. 19 is a block diagram of a measuring circuit including a voltage meter and a floating power supply according to one embodiment.

FIG. 19 is a block diagram of a measuring circuit 1900 including a voltage meter 1910 and a floating power supply 1912 according to one embodiment. The circuit 1900 includes two grounds electrically coupled through a range resistor Rr. The first ground is a signal ground to which the working electrode 116 is directly connected. The second ground is a power ground. When ion current flows from the working electrode 116 to the power ground, a voltage develops in the range resistor Rr that is measured by the grounded voltage meter 1910. The zero point of the power supply system kept on the working electrode potential by, for example, creating a virtual zero potential using a voltage follower.

The circuit 1900 allows the working electrode 116 to remain on true ground and the circuit 1900 is not sensitive to noise. The circuit 1900 also advantageously provides a grounded voltage meter 1910.

C. Active Current Shunt Circuit

Figure 20:
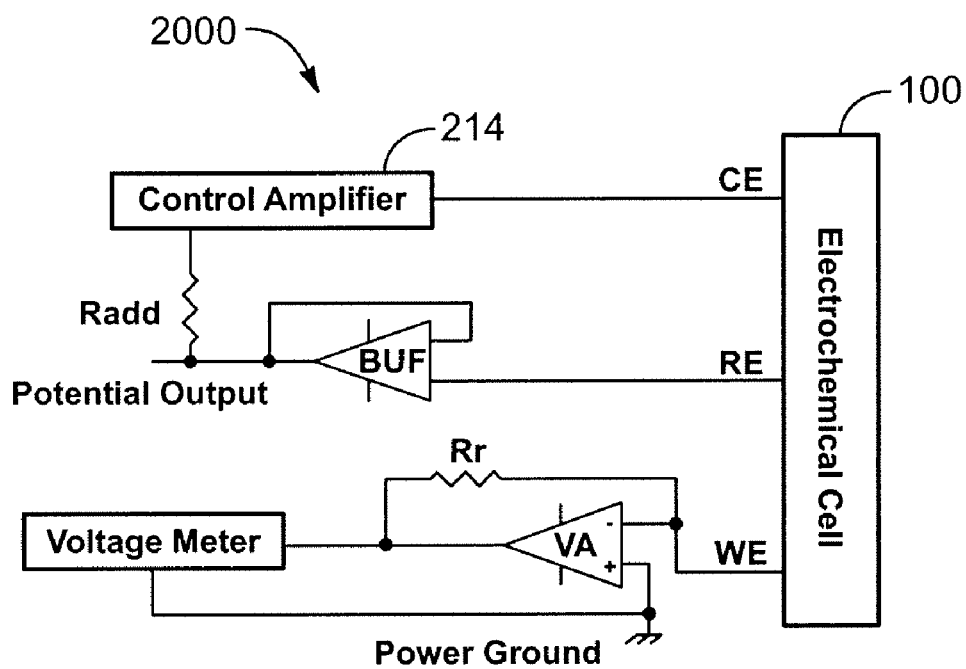
FIG. 20 is a block diagram of a measuring circuit that provides an active current sink according to one embodiment.

FIG. 20 is a block diagram of a measuring circuit 2000 that provides an active current sink according to one embodiment. The active current sink is a current-voltage converter that measures the current passing through a shunt. Very high-ohmic resistors may be used as the range resistor Rr. Thus, very low current can be precisely measured. The circuit 2000 also advantageously provides a voltage meter that refers to ground. However, the working electrode 116 is not really grounded and the circuit 2000 may be sensitive to noise.

D. Cable Selection to Avoid Triboelectric Noise Current

Generally, triboelectric current is generated in a cable by charges created at an interface between a conductor and an insulator due to friction. Free electrons rub off the conductor and create a charge imbalance that causes a current flow. Piezoelectric currents are generated when mechanical stress is applied to certain insulating materials. These currents are generated in ceramics and other crystalline materials used for insulating and material interconnection. Similar stored charges occur in many plastics.

In one embodiment, STFF-46 low noise coaxial cable available from Shanghai Jin ER Wire and Cable Co., LTD. of Shanghai, China is used as probe cables and for interconnection wire within the low current amplifier 218. The noise of this coaxial cable is approximately 4 to 5 scales lower than ordinary coaxial cable.

E. PCB Clearing

Noise currents also arise from electrochemical effects. For example, commonly used epoxy printed circuit boards may generate currents of several nanoamperes when not thoroughly cleaned of etching solution, flux or other chemicals and moisture. To reduce or prevent these error currents, all interconnecting circuits should be thoroughly cleaned and then be allowed to dry completely.

F. Guarding

High impedance paths between low current conductors and voltages sources (e.g., the path through the reference electrode 114) can cause significant leakage currents. Thus, in one embodiment, leakage currents through the reference electrode 114 and other high impedance paths are reduced or eliminated through guarding. Guarding uses a conductor at the same potential as the sensitive current path to totally surround the input leads carrying the high impedance signals. Guarding drastically reduces leakage currents from those leads.

Figure 21:
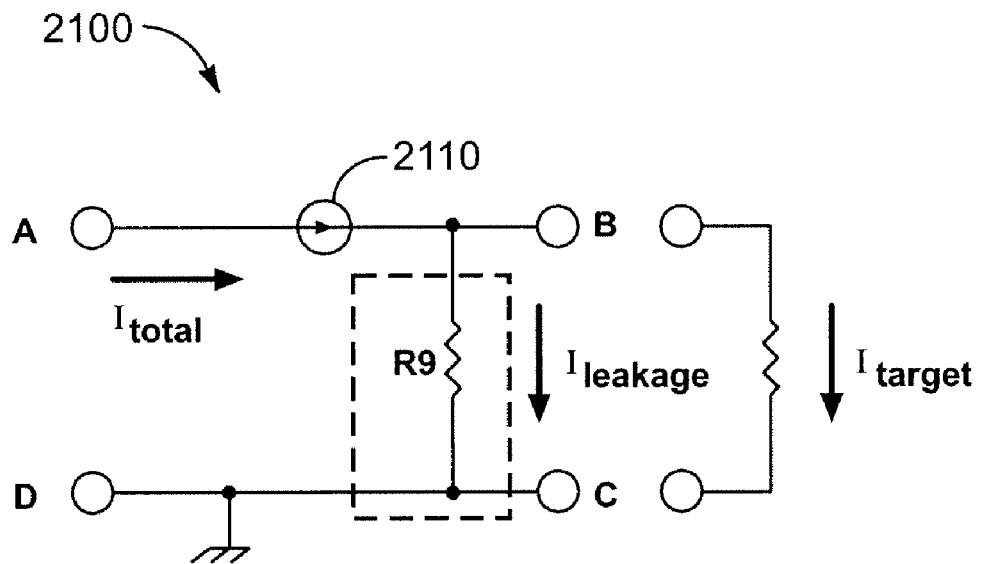
FIG. 21 is a schematic diagram of a circuit without guarding used to measure a current according to one embodiment.

For example, FIG. 21 is a schematic diagram of a circuit 2100 without guarding used to measure a current according to one embodiment. The circuit 2100 in this example includes an ammeter 2110 configured to measure a current $I_{target}$ flowing through the points A-B-C-D. Because of the existence of leakage current $I_{leakage}$, the total current $I_{total}=I_{target}+I_{leakage}$. If, for example, the potential of point B is 5V and $R9=10^9$ Ohms, then the leakage current leakage will be 5 nA. If the target current $I_{target}$ is on the order of or less than 5 nA, it will be overwhelmed by the leakage current $I_{leakage}$. In one embodiment, this problem is solved by increasing the leakage resistance R9 to approximately $10^{12}$ Ohms, which reduces the leakage current $I_{leakage}$ to approximately 5 pA. In some applications, 5 pA still may be large compared to the target current $I_{target}$.

Figure 22:
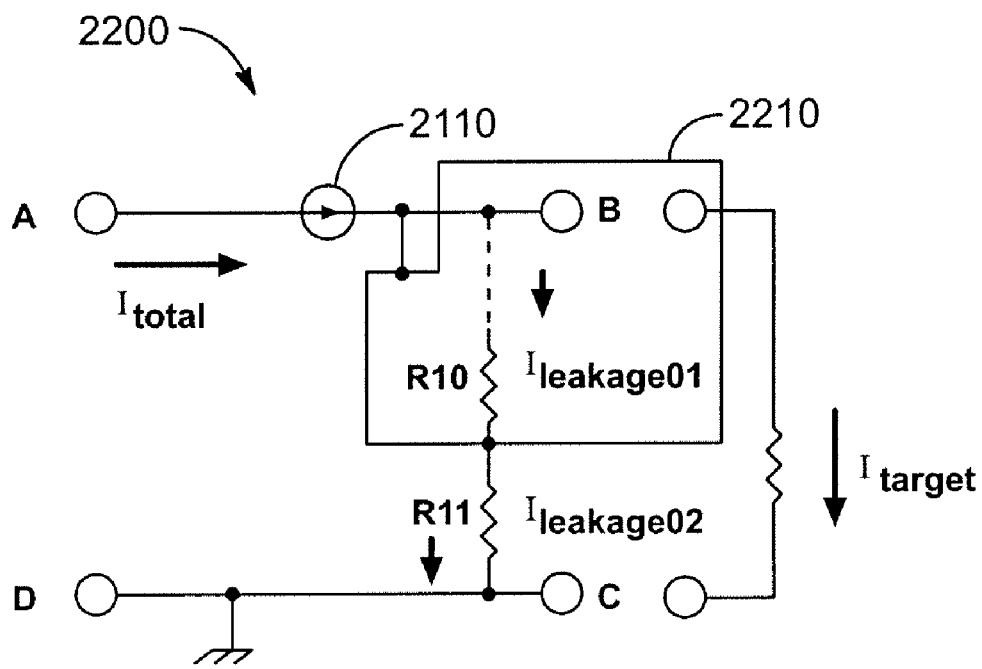
FIG. 22 is a schematic diagram of a circuit with guarding used to measure a current according to one embodiment.

FIG. 22 is a schematic diagram of a circuit 2200 with guarding used to measure a current according to one embodiment. The circuit 2200 is configured to reduce the effects of leakage currents by guarding the connection between the point B and the ammeter 2110. This portion of the circuit 2200 is completely surrounded by an electrical conductor 2210 connected to the same potential as that of point B. The resistance R9 shown in FIG. 21 is represented in FIG. 22 as resistances R10 and R11. In a coaxial cable, for example, R10 may represent a resistance between the cable's insulator and the cable's conductor, and R11 may represent the resistance between the cable's insulator and signal ground.

As shown in FIG. 22, the node between the resistance R10 and the resistance R11 is electrically coupled to the electrical conductor 2210. Because the electrical connector 2210 is also coupled to point A (through the ammeter 2110), the node between the resistances R10 and R11 has approximately the same electric potential as the point A. Thus, the potential difference across the resistance R10 is substantially equal to the voltage burden of the ammeter 2110. Because the typical feedback ammeter 2110 has a maximum voltage burden of approximately 200 µV, the leakage current may be reduced by approximately four decades. Assuming, for example, that the resistance R10 has the same value as that of resistor R9 above (e.g., approximately $10^9$ Ohms), the leakage current $I_{leakage01}$ through the resistance R10 is reduced to approximately 0.2 pA.

The resistance R11 is coupled between the node (e.g., the cable's insulator) and the point C (e.g., the signal ground) to complete the leakage path. Again, assuming that the resistance R11 is equal to the resistor R9 above (e.g., approximately $10^9$ Ohms) and the potential of point B is 5V, a leakage current $I_{leakage02}$ flowing through the resistance R11 is still approximately 5 nA. However, the leakage $I_{leakage02}$ is now supplied by a low impedance source (e.g., the 5V source) and is not a problem because it is not measured by the ammeter 2110.

Guarding may be provided, for example, in coaxial cables. When a probe cable, for example, has a high input impedance $R_s$ compared to a leakage resistance R, and the shielding layer is grounded, the measured voltage is:

$$\frac{R}{R+R_s} \times V_i.$$

When the shielding layer is connected to a low impedance source of the same potential as the high impedance source $V_i$, leakage current from the center conductor to the shield will vanish or be reduced. Then, the measured voltage will be approximately equal to $V_i$.

G. Example Current Amplifier Circuit Implementation

Figure 23:
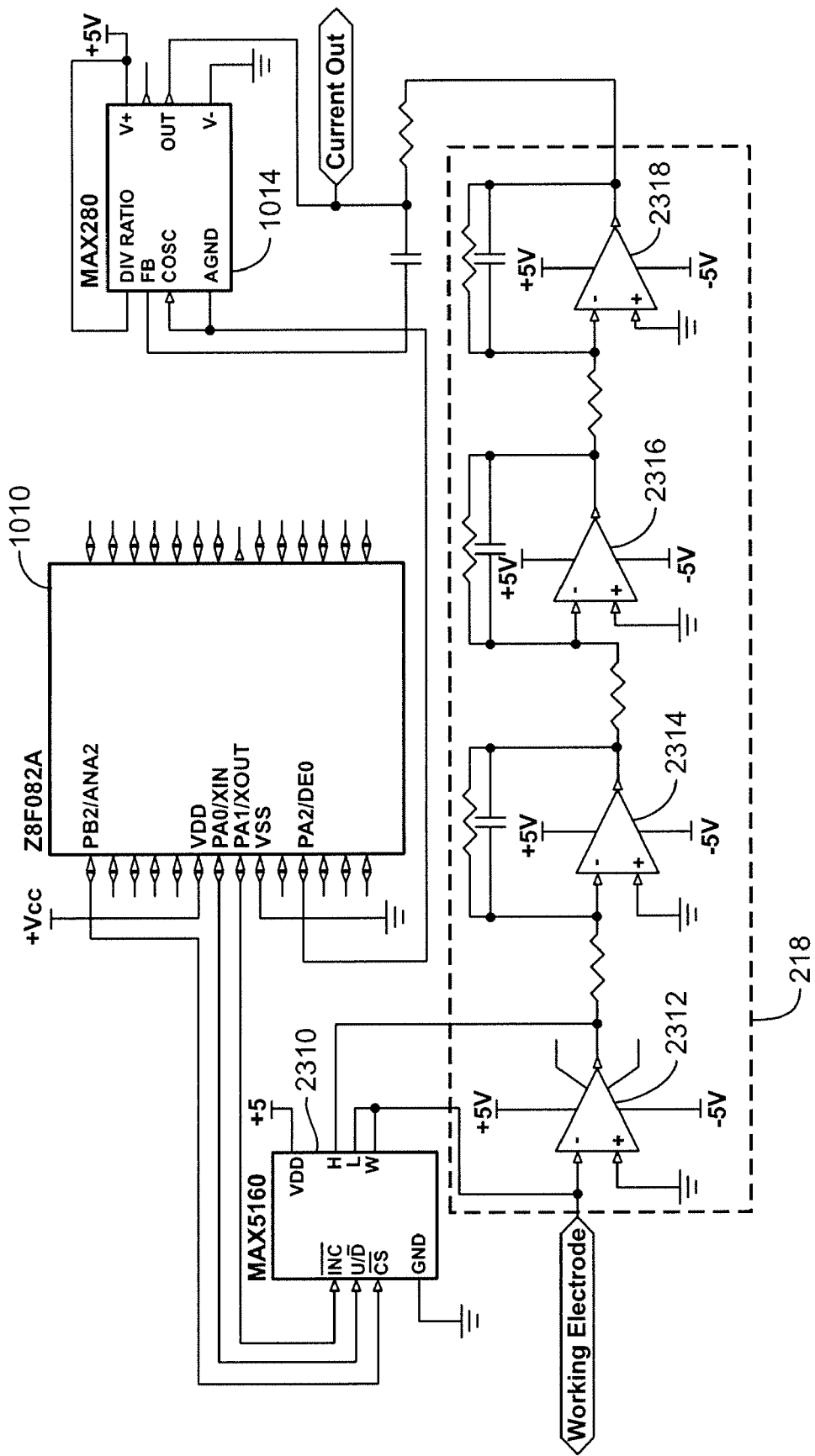
FIG. 23 is a schematic diagram of an example current amplifier circuit according to one embodiment.

FIG. 23 is a schematic diagram of an example current amplifier circuit 218 according to one embodiment. The circuit 218 is controlled by the example Z8 F082A microprocessor 1010 discussed above. The current amplifier circuit 218 is also electrically connected to the MAX280 LPF 1014 discussed above.

To meet the dynamic range, the current amplifier circuit 218 includes a two stage current follower including the operational amplifiers 2312, 2314, 2316, 2318. The gain of a first stage of the current follower may be adjusted by the microcontroller 1010. In one embodiment, the maximum gain of the first stage is selectively set to approximately 80 dB and the gain of the second stage is unadjustable (e.g., set at approximately 60 dB). The fixed gain of the second stage may be based on the specific ion solution 110 being tested. In one embodiment, the total dynamic range is between approximately 60 dB and approximately 180 dB, including approximately 40 dB of fixed DC gain provided by the lock-in amplifier 222 (discussed in detail below).

As shown in FIG. 23, the current amplifier circuit 218 may be connected to the microcontroller 1010 through a MAX5160 linear-taper digital potentiometer 2310 available from Maxim Integrated Products, Inc. of Sunnyvale, Calif. The MAX5160 potentiometer 2310 performs the same function as a mechanical potentiometer or a variable resistor. The MAX5160 potentiometer 2310 includes a fixed resistor and a wiper contact with 32 tap points that are digitally controlled by the microcontroller 1010. The MAX5160 potentiometer 2310 is configured to selectively adjust the gain of the current amplifier 218.

V. Example Lock-In Amplifier Embodiments

The lock-in amplifier 222 (see FIG. 2) is configured to remove or reduce noise from a target signal to be measured. A high speed digital clock (e.g., used by the DDFS) and other circuit components may introduce broadband noise. The measured target signal is the ion current flowing through the electrochemical cell 100, which may be weak enough to sometimes be buried completely by the broadband noise. Generally, the dynamic of the target current will reach approximately 4 decades, from approximately 100 pA to approximately 2 mA.

Figure 24:
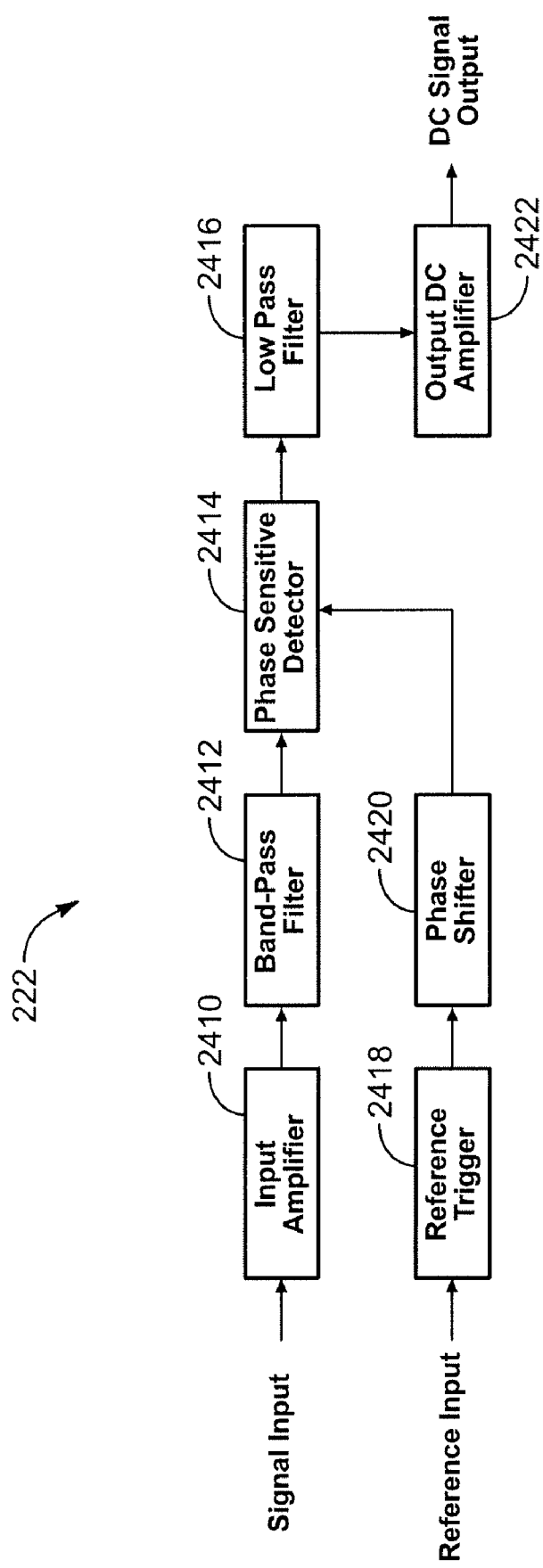
FIG. 24 is a block diagram of a lock-in amplifier according to one embodiment.

FIG. 24 is a block diagram of a lock-in amplifier 222 according to one embodiment. The lock-in amplifier 222 includes an input amplifier 2410 configured to receive a signal input, a band-pass filter 2412, a phase sensitive detector (PSD) 2414, a low-pass filter 2416, a reference trigger 2418 configured to receive a reference input, a phase shifter 2420, and an output DC amplifier 2422 configured to provide a DC signal output. An active current shunt acts as a current to voltage converter the current of the signal input (e.g., on a pA scale) is pre-amplified and transformed to a voltage (e.g., on the nV scale) on the DC signal output.

Assume, for example, that $X(t)$ is a period target signal $S(t)$ mixed with a random noise signal $N(t)$ where $X(t)=S(t)+N(t)=A \sin(\omega t+\varphi)+N(t)$. The reference input signal is given by $Y(t)=B \sin \omega(t+\tau)$, where $\tau$ is a time offset. A correlations function $R_{xy}$ of mixed signal $X(t)$ and reference signal $Y(t)$ is $$R_{XY} = \lim_{T \to \infty} \frac{1}{T} \int_0^T B\sin\omega(t+\tau)[A\sin(\omega t+\varphi) + N(t)]dt$$

$$= \frac{AB}{2}\cos(\omega t + \varphi) + R_{NY}(\tau)$$

$$= \frac{AB}{2}\cos(\omega \tau + \varphi).$$

Because the noise signal $N(t)$ is non-correlated with the reference signal $Y(t)$, $R_{NY}(\tau)=0$. Thus, $R_{XY}$ is a DC value and proportional to the amplitude of the target signal input and the reference signal input.

In one embodiment, the PSD 2414 comprises a demodulator. The PSD 2414 operates by multiplying two signals together. For example, assume that the target input signal is $U_s = E_s \times \sin(2 \times \pi \times f_1 \times t + \phi_1)$ and that the reference input signal is $U_r = E_r \times \sin(2 \times \pi \times f_2 \times t + \phi_2)$, the PSD 2414 is configured to multiply these two signals to provide $$U_{out} = U_s \times U_r$$

$$= \frac{E_s E_r}{2}\cos[2\pi(f_1 - f_2)t + (\varphi_1 - \varphi_2)] -$$

$$\frac{E_s E_r}{2}\cos[2\pi(f_1 + f_2)t + (\varphi_1 + \varphi_2)].$$

The output of the PSD 2414 includes two parts. One part is a frequency sum of the target signal input and the reference input signal. The other part is a frequency difference of the target signal input and the reference input signal. When $f_1=f_2$, the difference part converts to a DC component of the PSD's output, and the sum part has exactly twice the frequency of the input signal, which may be isolated by the low-pass filter 2416.

In one embodiment, a symmetrical square wave may be used as the reference input signal. A Fourier series representation of the reference input signal may be given by $$U_r = \frac{4}{\pi}\sum_{n=0}^{\infty}\frac{1}{2n+1}\sin[(2n+1)(2\pi f_2 + \varphi_2)].$$

The output of the PSD 2414 may be given by $$U_o = \frac{2E_s}{\pi}\sum_{n=0}^{\infty}\frac{1}{2n+1}\cos\{2\pi[f_1 \pm (2n+1)f_2]t + [\varphi_1 \pm (2n+1)\varphi_2]\}.$$

If $$f_1 = f_2, U_o = \frac{2E_s}{\pi}\sum_{n=0}^{\infty}\frac{1}{2n+1}\cos[\varphi_1 \pm (2n+1)\varphi_2],$$

assume $\theta=\phi_1-\phi_2$, and with the help of the low pass filter 2416, $$U_o = \frac{2E_s}{\pi}\cos\theta,$$

then the amplitude is given by $$|U_s| = \frac{U_o \pi}{2\cos\theta}.$$

The above discussion is based on the case of a noise-free input signal. If noise is presented on the input signal, which has no fixed frequency or phase relationship with the reference input, it is also multiplied by the reference input signal in a modulator, but does not result in any change to the mean DC level. Thus, the combination of the PSD 2414 and the low pass filter 2416 allows signals to be measured even when accompanied by significant noise.

A. Example Lock-In Amplifier Circuit Implementation

Figure 25:
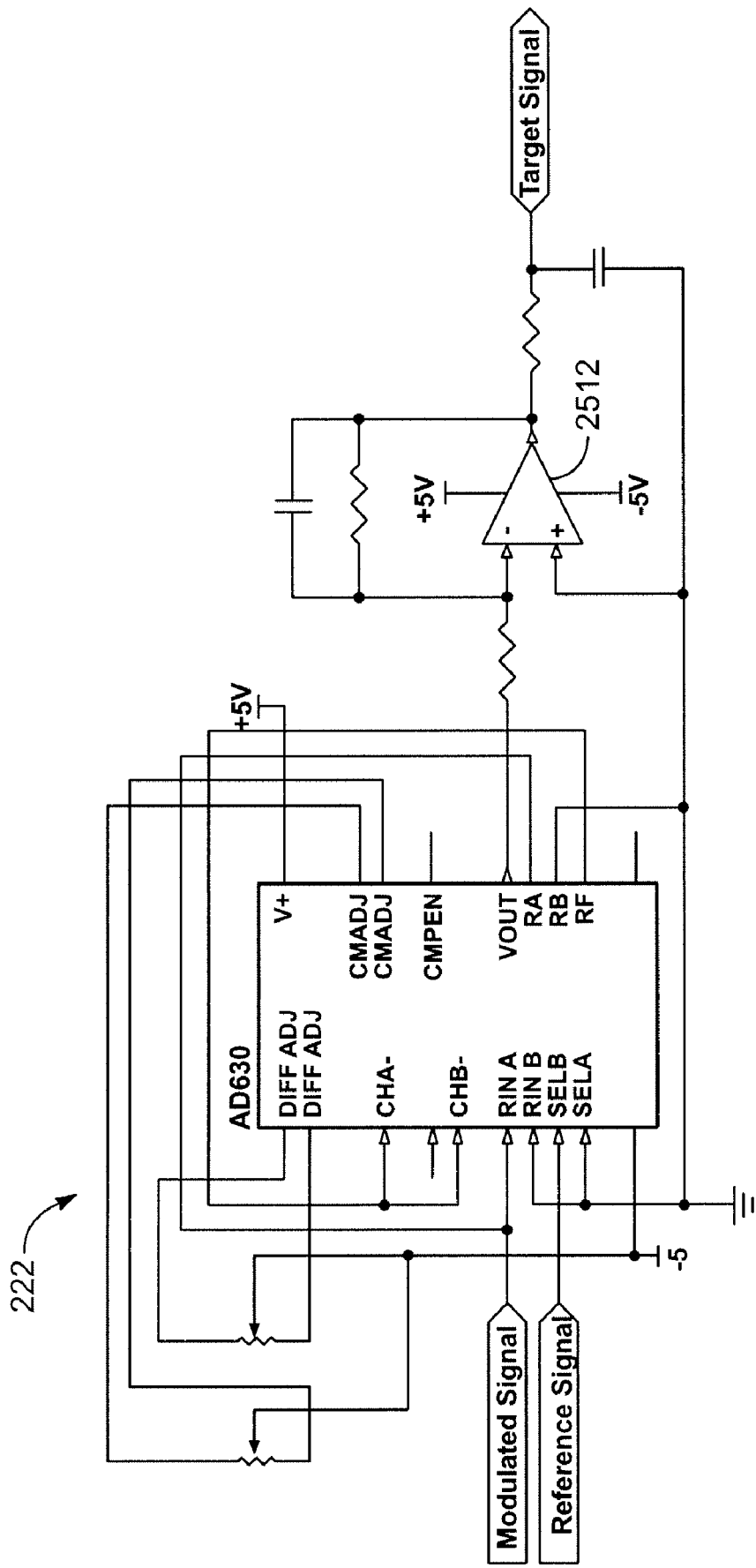
FIG. 25 is a schematic diagram of an example lock-in amplifier circuit according to one embodiment.

FIG. 25 is a schematic diagram of an example lock-in amplifier circuit 222 according to one embodiment. The circuit 222 includes an AD630 high precision balanced modulator/demodulator 2510 available from Analog Devices, Inc. of Norwood, Mass. The AD630's signal processing applications include phase detection and may be used to realize a lock-in amplifier with working frequency up to several hundred kilohertz. The AD630 may be thought of as a precision operational amplifier with two independent differential input stages and a precision comparator which is used to select an active end.

A commonly used application of the AD630 is the balanced modulator/demodulator. By setting $R_B/R_F/R_A$, the AD630 provides precise symmetric gain of ±1 dB and ±2 dB. The balanced modulator/demodulator topologies accept two inputs, a signal input applied to the amplifying channels, and a reference input applied to the comparator. The modulated signal is the output voltage signal of active current shunt, which includes background noise and the ion current signal. The reference signal comes from a 0.5 Hz oscillator. This reference signal is also added to the summing circuit of the control amplifier 214. The noise modulated current-voltage signal is demodulated synchronously using phase information derived from the modulator, and the result is low-pass filtering using a 2-pole simple filter, which also provides a DC gain of approximately 100 dB to the output. The precision input performance of the AD630 provides more than 100 dB of signal range.

VI. Measurement and Control

Figure 26:
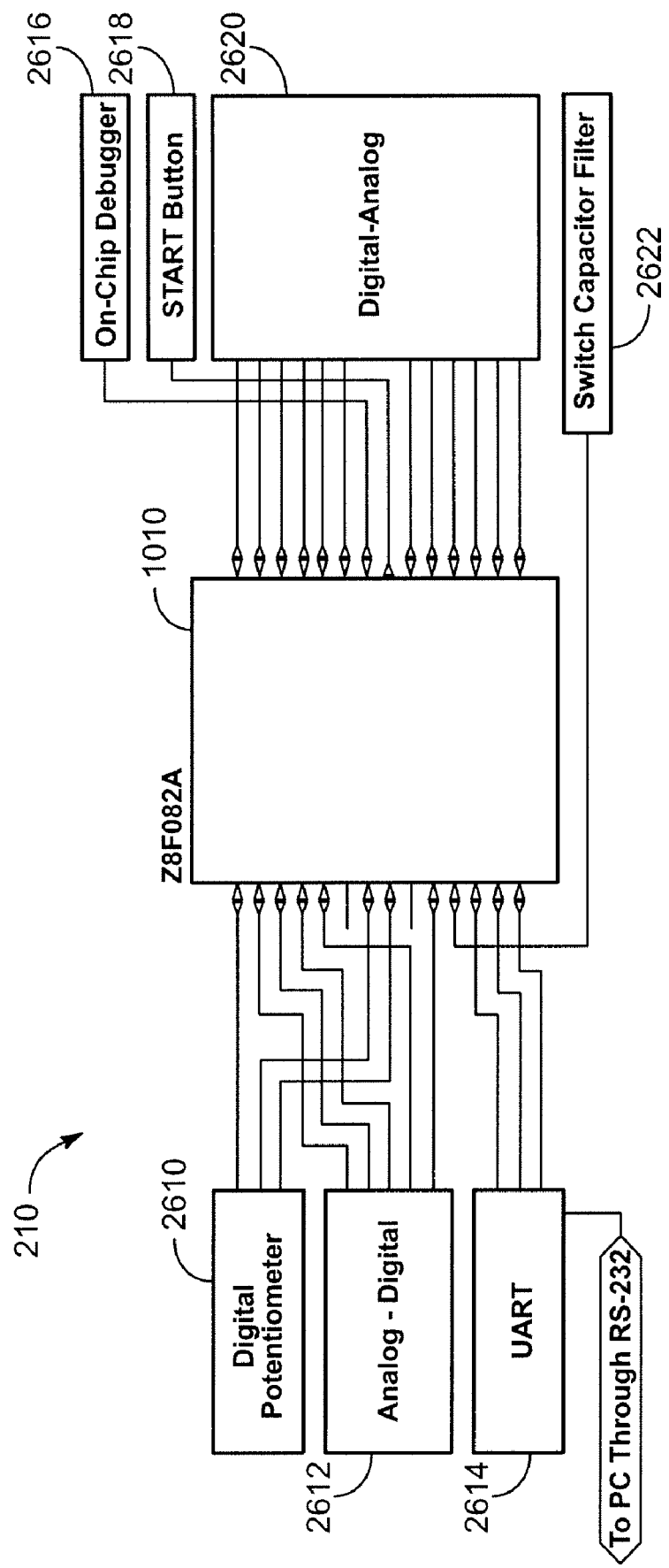
FIG. 26 is a block diagram of a measurement and control unit shown in FIG. 2 according to one embodiment.

FIG. 26 is a block diagram of the MAC unit 210 shown in FIG. 2 according to one embodiment. The MAC unit 210 may include a microprocessor 1010, a digital potentiometer 2610, an analog-to-digital converter (ADC) 2612, a UART 2614, an on-chip debugger 2616, a start button 2618, a digital-to-analog converter (DAC) 2620, and a switch capacitor filter 2622.

As discussed above, the measurement and control of the electrochemical chip 200, along with other function modules such as sweep wave generator, time base of switch capacitor filter, and interface with a host computer, is based on the 8-bit Zilog microprocessor 1010, Z8 Encore F082A. This microcontroller 1010 incorporates a rich peripheral set and makes it suitable for a variety of applications including sensor network, motor control and other applications. The 28-pin package Z8 F082A supports a maximum of 25 port pins for general-purpose input/output operation. This is convenient for the interconnection with each function module. The interconnection with DAC unit 2620, the switch capacitor unit 2622, and the digital potentiometer unit 2610 has been previously illustrated.

A. Example Analog-Digital Unit

The on-chip ADC 2612 converts an analog input signal to its digital representation. In one embodiment, the on-chip ADC 2612 provides 10-bit resolution in signal-ended mode, 8 signal-ended analog input sources, interrupt upon conversion complete, and manual n-circuit calibration employing user code.

There are two channels of analog voltage that are monitored. The first channel includes a potential value from the control amplifier 214, which is connected to pin2/ANA7 of the microcontroller 1010. The second channel includes a differential current value from the current amplifier 218, which is connected to pin4/ANA3 of the microcontroller 1010. The differential current value is measured at the end of each half-cycle and the current measured in the reversed half cycle is subtracted from the current measured on the forward half-cycle. In one embodiment, these sampled potential and differential current values are sent to a host computer (e.g., through an RS232 or USB interface).

B. UART Unit

In one embodiment, the on-chip UART unit 2614 is a full-duplex communication channel capable of handling asynchronous data transfers. The UART 2614 uses a single 8-bit data mode with selectable parity. Separate transmit and receive interrupts may be initialized.

Figure 27A:
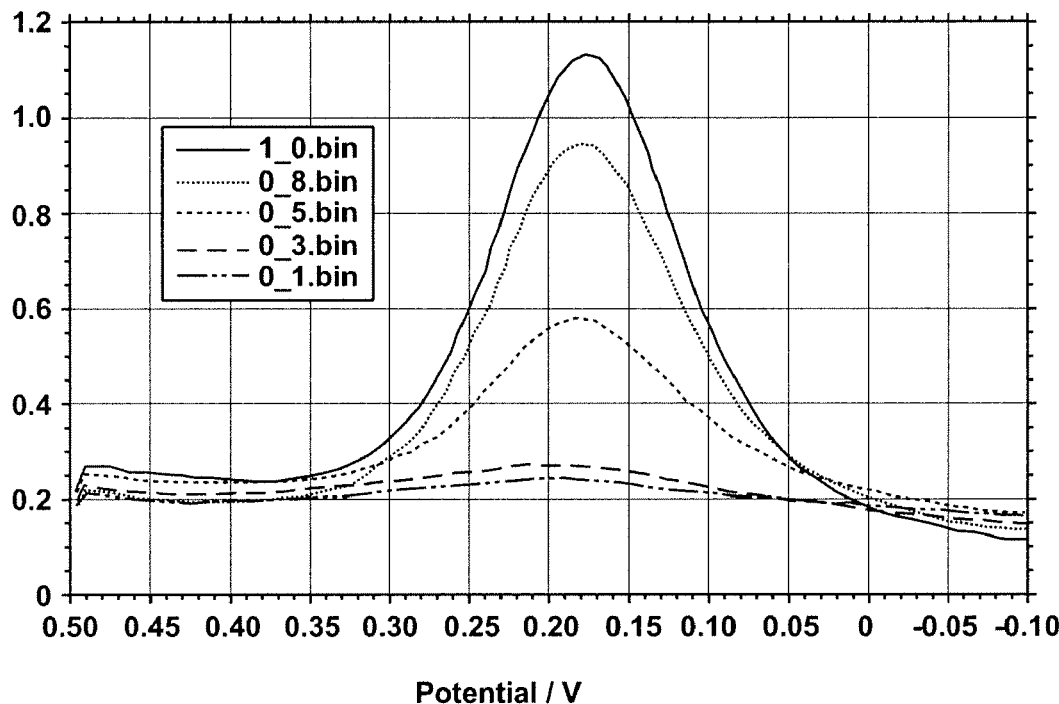
FIG. 27A schematically illustrates square wave voltammetry (SWV) responses to various $K_3Fe(CN)_6$ solutions using a conventional electrochemical instrument.

VII. Example Measurements with Conventional and New Electrochemical Measurement Systems To verify the systems and methods disclosed herein, the electrochemical chip 200 was tested using cyclic voltammetric measurements with approximately 2 mm gold electrodes in a $K_3Fe(CN)_6$ solution, which is an electrochemical standard. The test results were compared to results obtained from a conventional electrochemical instrument. For example, FIG. 27A schematically illustrates SWV responses to various $K_3Fe(CN)_6$ solutions using a conventional electrochemical instrument. For this test, the conventional electrochemical instrument included a CHI 1220 electrochemical analyzer available from CH Instruments, Inc. of Austin, Tex. that was used to test 0.01 M phosphate buffered solutions (PBS, pH 7.4) with various $K_3Fe(CN)_6$ concentrations (0.1 mM, 0.3 mM, 0.5 mM, 0.5 mM, 0.8 mM, and 1.0 mM).

Figure 27B:
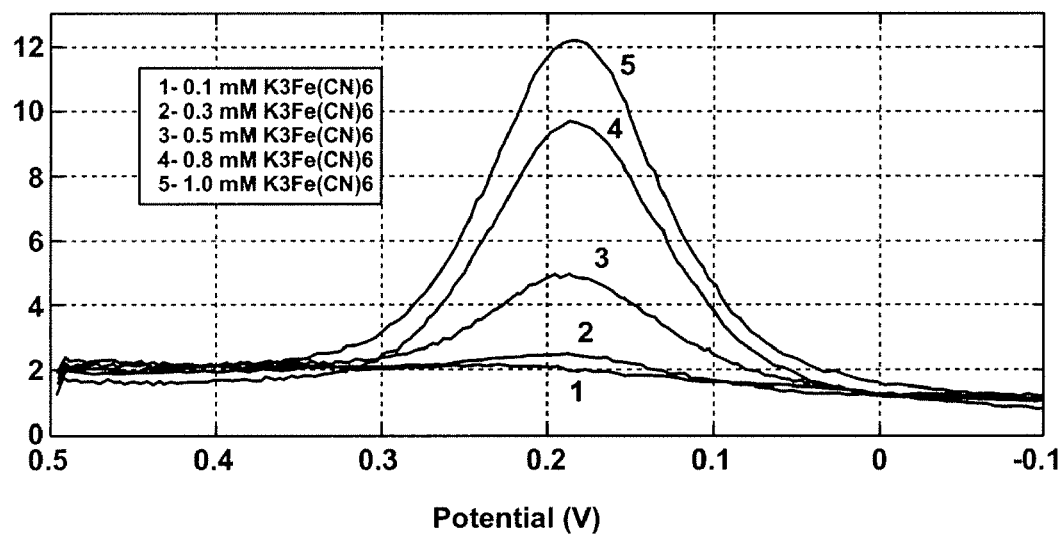
FIG. 27B schematically illustrates SWV responses to the same $K_3Fe(CN)_6$ solutions discussed with respect to FIG. 27A using the electrochemical chip disclosed herein.

By way of comparison with the waveforms shown in FIG. 27A, FIG. 27B schematically illustrates SWV responses to the same $K_3Fe(CN)_6$ concentrations discussed n FIG. 27A by the electrochemical chip 200 disclosed herein with the same 2 mm gold electrodes. As shown, the SWV curves in FIG. 27B are very similar to the SWV curves in FIG. 27A, confirming the accuracy of the systems and methods described herein.

FIG. 27C schematically illustrates data combined from FIGS. 27A and 27B to further illustrate the consistency of responses from conventional electrochemical instruments and the systems and methods disclosed herein. FIG. 27C is the comparison of the peak currents vs. the concentrations of $K_3Fe(CN)_6$. In FIG. 27C, data generated by the electrochemical chip 200 is illustrated as plus ("+") marks and data generated by the conventional electrochemical instrument (CHI 1220) is illustrated as circles ("O"). In this example, the SWV parameter settings are the same for both instruments and the data corresponds to the same $K_3Fe(CN)_6$ concentrations (0.1 mM, 0.3 mM, 0.5 mM, 0.5 mM, 0.8 mM, and 1.0 mM) discussed above. As shown in FIG. 27C, the electrochemical chip 200 disclosed herein provides data that corresponds very closely to the data provided by the conventional electrochemical instrument. Further, the electrochemical chip 200 provides a straighter calibration curve between approximately 0.3 mM and approximately 1.0 mM than that provided by the conventional electrochemical instrument. Thus, the electrochemical chip 200 provides better linearity in this range than that provided by the conventional electrochemical instrument.

In addition to testing $K_3Fe(CN)_6$ solutions (see FIGS. 32-33), the microelectrodes disclosed herein were used to test standard solutions of varying metals Pb, Zn, and Cu using ASV (using a conventional (e.g., CHI 1220 Electrochemical Analyzer). Example test results are discussed below (see FIGS. 34-40).

VIII. Example Microelectrode Array Sensor

In one embodiment, the electrochemical chip 200 may be used with one or more microelectrode arrays that include individualized gold working electrodes 116 strategically arranged in an array fashion to detect heavy metal ions in aqueous solutions. Utilizing micron sized microelectrodes in a geometric array has been shown to improve mass transport, thus improving the sensitivity and selectivity of the gold microelectrodes. In one embodiment, these arrays have the capability to run as individually addressable microelectrodes while performing numerous tests in a single experimentation, or to run as one electrode increasing the overall surface area of the electrode. In addition, or in another embodiment, the arrays provide some intermediate partial individualization and partial colonization of the electrodes.

In one embodiment, the microelectrode arrays are quantified by, and proven with, electrochemical standardizing potassium ferric cyanide (PFC) solution and cyclic voltammetry (CV). Using this standard, high sensitivity, selectivity, and repeatability have been shown. Heavy metal ion detection is preformed with the anodic stripping voltammetry (ASV) electrochemical test and trace levels of copper, lead, and zinc have been detected and standardized in aqueous solutions. Testing (discussed below) shows high specificity and accurate technique for heavy metal ion detection in aqueous solution.

Traditionally, heavy metal ion sensors associated with anodic stripping voltammetry (ASV) have been composed of macro-scale electrodes (e.g., radius of approximately 1 mm). ASV is a very accurate procedure in determination of trace metals in aqueous solution and with the initiation of micron sized electrode surface area, according to embodiments disclosed herein, trace amounts (e.g., parts-per-billion (ppb)) of metals can be detected in times less than approximately 3 minutes. Electrochemical testing in this nature (voltammetry) only requires a relationship between a potential and measured current, which in effect contributes to the analyzing instrument's ability to be small and compact. This improves portability of the entire testing process. Furthermore, utilizing a fabrication technology similar to that used with integrated circuits, these sensors may be constructed relatively inexpensively and reproducibly with precise geometries.

By decreasing the size of the electrode surface area to a micron state, according to certain embodiments, mass transport is dramatically enhanced. This increase in mass transport greatly improves the sensitivity and selectivity of the electrode, thus improving the device's versatility. Furthermore, micron sized electrodes in arrays enable the user to compare analytes in aqueous solution at varying geometric locations. In effect, this allows multiple repetitions of analyte detection during a single iteration of testing. Simultaneously, these microelectrodes can vary in measurement range, differing among the microelectrodes comprising the array, to detect multiple elements in one broad test. These combined factors make multiplex detection of trace metals at very low levels possible in highly accurate robust measurements.

In one embodiment, microelectrode arrays are constructed on a single glass slide, with each array including 18 microelectrodes. In certain such embodiments, these microelectrodes are approximately 10 μm by approximately 10 μm squares with approximately 100 μm distances between adjacent electrodes. An artisan will recognize, of course, that the microelectrodes need not be square and may be other shapes such as rectangular, circular, or any other shape. In one embodiment, approximately 100 times the width of the electrodes is the approximate minimum distance between adjacent working electrodes in order to maximize quantification of working electrode overpotential and impedance. In one embodiment, a protective layer of photoresist is heat set to provide hardness masking of all circuitry of the electrodes, also adding to greater quantification.

In one embodiment, the microelectrode arrays (MEA) are based on a planar design where approximately 10 μm by approximately 10 μm gold working electrodes are positioned (approximately 10 μm thick) on glass to form arrays. Adequate adherence to glass is accomplished by a thin (approximately 150 nm) layer of Titanium between the gold surface and the glass support base. In this example embodiment, glass was chosen as the support base for its low electrical conductivity.

FIGS. 28A-28B are schematic diagrams of nine microelectrodes arranged in respective half arrays 2810, 2812 according to certain embodiments. For illustrative purposes, FIGS. 28A and 28B are scaled differently with FIG. 28A being enlarged more than FIG. 28B. In this example, the approximate geometry of the microelectrodes and arrays are as follows: a 50 μm×50 μm base microelectrode with 30 μm wide circuitry to connect the microelectrode with an outer slide connection pad. An array includes 18 microelectrodes and a half array includes nine microelectrodes. For ease in fabrication, there are three central microelectrodes in a half array that have short spans of 10 μm wide connection circuitry. A final layer of photoresist masks the entire slide with exception of a 10 μm×10 μm hole allowed over each 50 μm×50 μm pad and the connection pads on the glass slide edges. The half array 2810 shown in FIG. 28A is illustrated before the final photoresist mask is applied and treated. The half array 2812 shown in FIG. 28B is illustrated after the final photoresist mask is applied and treated.

Figure 29:
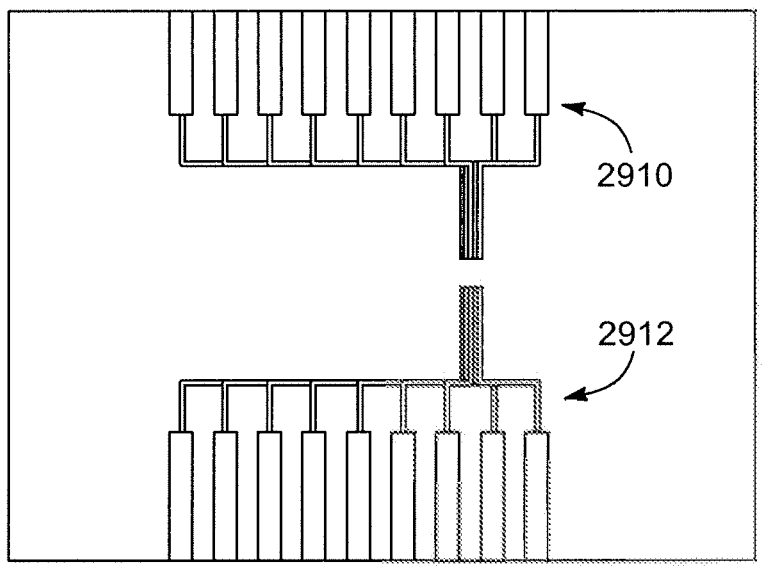
FIG. 29 is a schematic diagram of a completed array that illustrates connection pads and interconnection traces for a first half array of nine microelectrodes and a second half array of nine microelectrodes according to one embodiment.

FIG. 29 is a schematic diagram of a completed array that illustrates connection pads and interconnection traces for a first half array 2910 of nine microelectrodes and a second half array 2912 of nine microelectrodes according to one embodiment. Although not shown in FIG. 29, each half array 2910, 2912 includes the microelectrodes shown in FIG. 28B.

Figure 30:
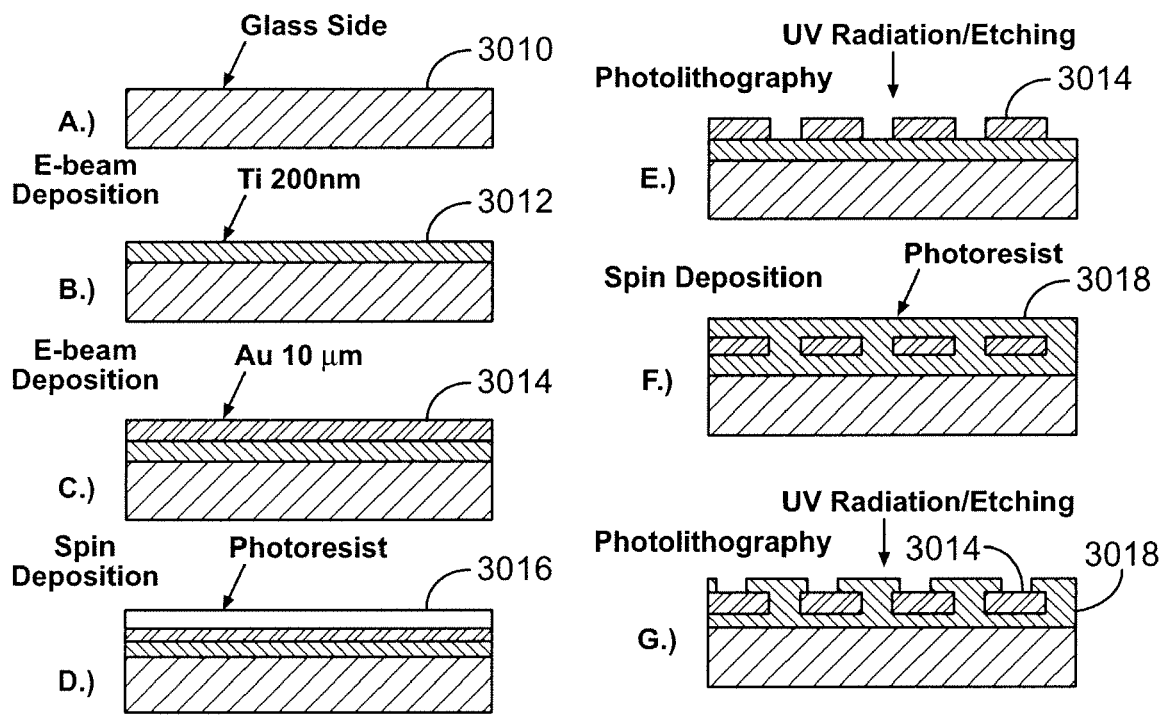
FIG. 30 is a schematic diagram of various steps in a process for manufacturing the microelectrode array shown in FIG. 29 using photolithography according to one embodiment.

FIG. 30 is a schematic diagram of various steps (steps A-G) in a process for manufacturing the microelectrode array shown in FIG. 29 using photolithography according to one embodiment. In step A, a glass slide 3010 is provided. In step B, a thin (e.g., approximately 200 nm thick) layer of Titanium 3012 is deposited onto the glass slide 3010. Rather than using a conventional chrome/gold layer deposited on the glass slide 3010, the layer of Titanium 3012 provides relatively stronger adhesion of a layer of gold 3014 (see step C) to the glass slide 3010. The improved adhesion allows a broader potential range that can be applied to the working electrode 116. In step C, the layer of gold 3014 (e.g., approximately 10 μm thick) is deposited onto the Titanium 3012. In step D, a photoresist layer 3016 is deposited onto the gold 3014. In steps E through G, the gold 3014 is then stripped to the geometries specified for the 18 individually isolated microelectrodes using a basic photolithography technique.

In one embodiment, the glass slides 3010 are completed with three arrays per slide 3010, giving a total of 54 individually isolated working microelectrodes per slide 3010. Another step (not shown in FIG. 30) includes an adhesion of wells cut from a 96 welled plate. In one embodiment, the wells are attached with the use of a non-conductive epoxy that does not effect the photoresist mask 3018 or the individual circuitry that comprises the microelectrode arrays.

Figure 31:
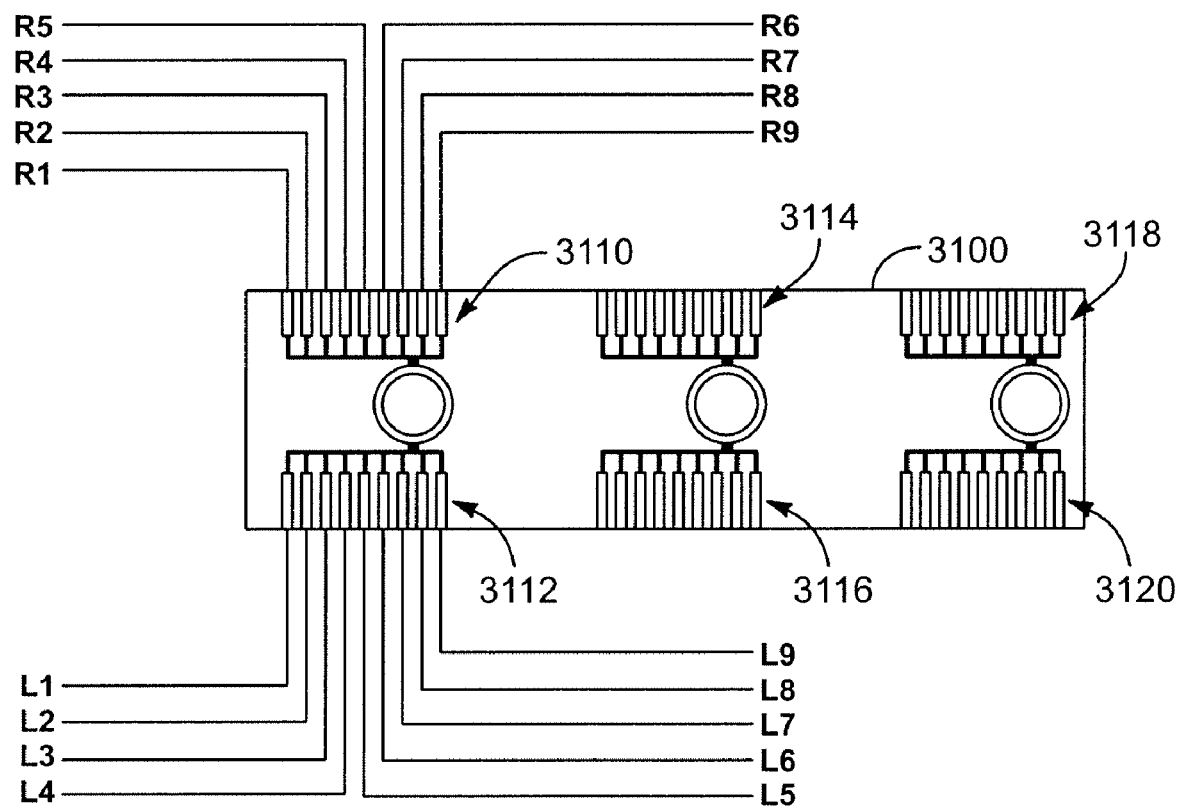
FIG. 31 is a schematic diagram of a finished glass slide with individual microelectrodes comprising three arrays respectively corresponding to three wells according to one embodiment.

FIG. 31 is a schematic diagram of a finished glass slide 3100 with the individual microelectrodes (shown in detail in FIG. 28B) comprising the three arrays respectively corresponding to three wells (each schematically represented as a pair of concentric circles) according to one embodiment. Each array is respectively organized in respective half arrays 3110, 3112, 3114, 3116, 3118, 3120 that each include nine microelectrodes. FIG. 31 also illustrates a numbering scheme (R1-R9 and L1-L9) developed to label each array.

IX. Example Experiments

The following disclosure relates to example experiments performed using the systems and methods disclosed herein. In these example experiments, photolithographic techniques were used to fabricate single element gold microelectrode arrays with 18 individually isolated 10 μm×10 μm gold microelectrodes in a single array. These arrays were orientated to work individually or simultaneously on a single glass slide. Initial tests were conducted using PFC as a standard to test the array's capacity to be used with electrochemical tests. This standard is widely utilized for calibration of fabricated microelectrodes. CV was used as the electrochemical test which applies a sweep potential that goes from a negative state to a positive state and then cycles back from positive to negative. Throughout the sweep, potential current changes were monitored and (along with standardized solutions) are used to quantify the microelectrodes.

ASV is another electrochemical method of testing for heavy metal ions in solution. ASV is performed by applying a constant negative potential for a predetermined amount of time and then sweeping the potential towards a positive region. As the potential is being swept from negative to positive, the current changes are monitored. The sweeping mechanism may vary. In these example experiments a differential pulse mechanism is used for sweeping. ASV that uses a differential pulse sweeping mechanism is known as DPSV.

Heavy metal ion detection is possible due to positive charged ions attaching to the electrode surface during the initial negative potential charge. As the sweeping potential moves towards a positive region, the ions disperse off of the electrode surface at a characteristic potential. Each ion has a distinct characteristic potential that is used to identify it in the solution.

In these example experiments, the microelectrode arrays are used to detect traces of Cu, Pb, and Zn ions in varied concentrations of solution. In one embodiment, the example experiments accurately and reproducibly detect Cu, Pb, and Zn ions at a sensitivity of approximately 1 ppb in an aqueous solution.

The materials and methods used in these example experiments may be summarized as: photolithography; Denton E-Beam evaporator; Electromask pattern generator and image repeater; Suss spinner/aligner; EV 420 front and backside aligner; and 1813 Photoresist. The electrochemical parameters of these example experiments may be summarized as: CHI 1220 electrochemical analyzer (CH Instruments, TX) and corresponding control software; 18 microelectrode Au array with Ag/AgCl reference microelectrodes and platinum wire counter microelectrodes; potassium ferricyanide (K3Fe(CN)6) solution in 0.01 M PBS, 18MΩcm (DI) water, and 1,000 ppm Cu reference solution (Fishersci, Inc.); and PlasmaLab MicroP reactive ion etch.

A. Experimental Results

As discussed above with respect to FIGS. 30 and 31, the process used for fabrication of the microelectrode arrays for these example experiments is a photolithographic procedure. FIG. 30 shows a generalized procedure using photolithography where the process is highly repeatable and accurate to small (e.g., approximately 1-5 μm) limits. FIG. 31 shows a completed slide and the microelectrode numbering scheme for each of three wells on a glass slide. These microelectrodes constitute the arrays that make up a single test site.

Figure 32:
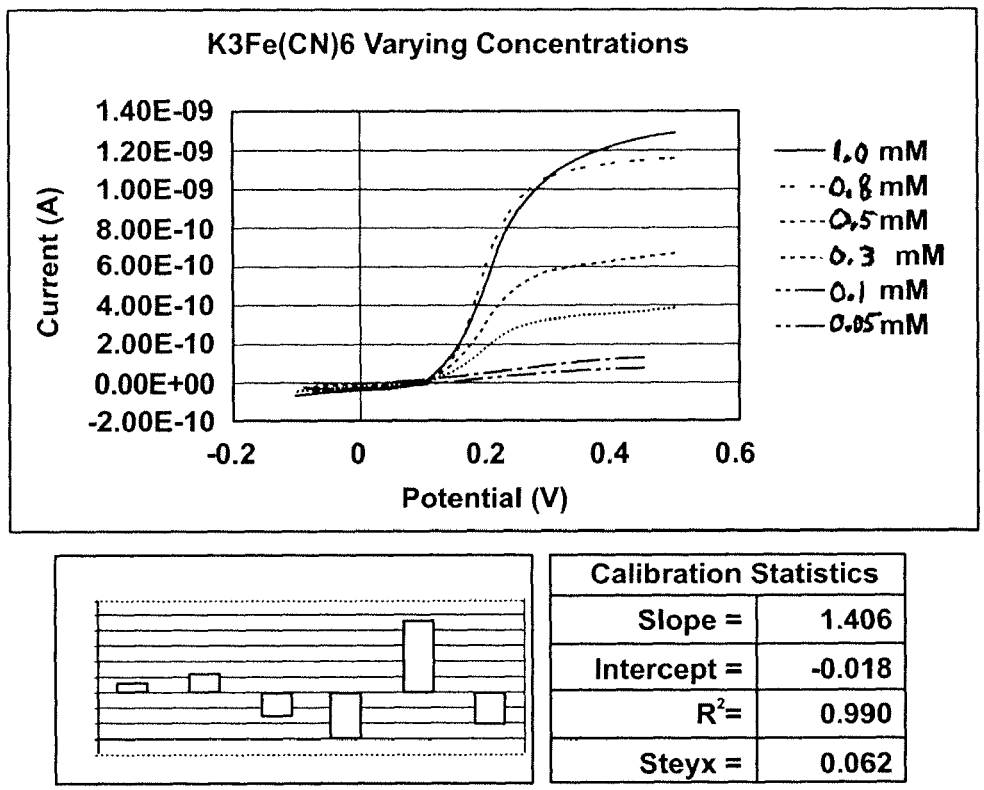
FIGS. 32-33 graphically illustrate results of testing microelectrodes disclosed herein in Potassium Ferric Cyanide ($K_3Fe(CN)_6$) using cyclic voltammetry.
Figure 33:
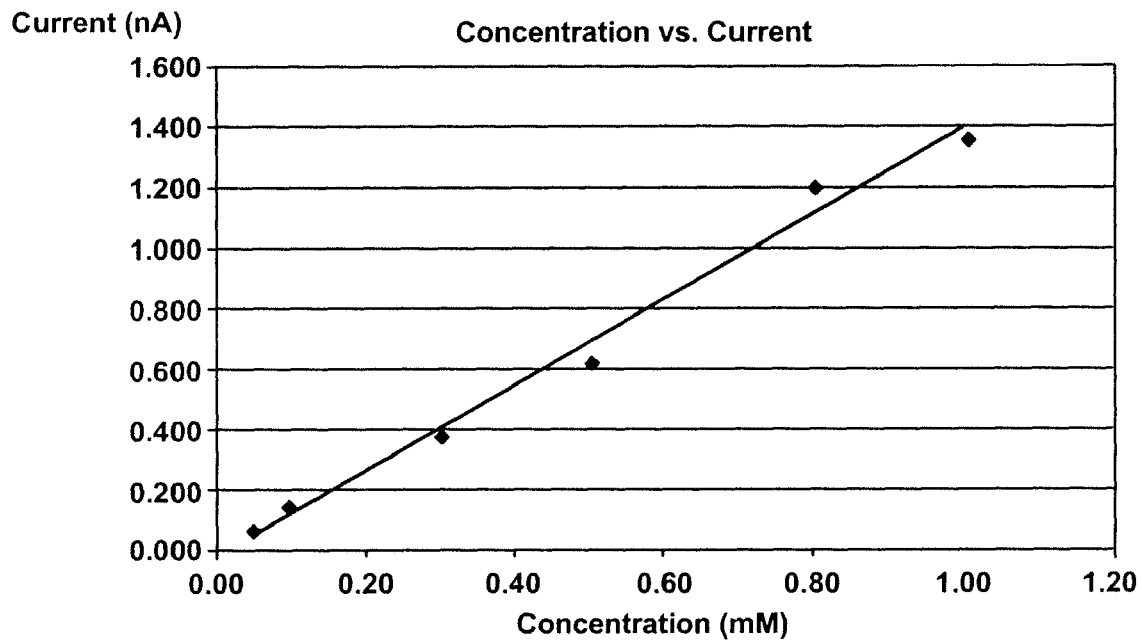

FIGS. 32-33 graphically illustrate results of initially testing the microelectrodes disclosed herein in Potassium Ferric Cyanide ($K_3Fe(CN)_6$) using cyclic voltammetry. As shown in FIG. 33, there is a distinct linear relationship between concentration and change in height (e.g., current) in CV analysis. This result indicates that the microelectrodes are working well. Although not shown, the test also indicated that each microelectrode produces substantially the same results at a constant concentration.

Figure 34:
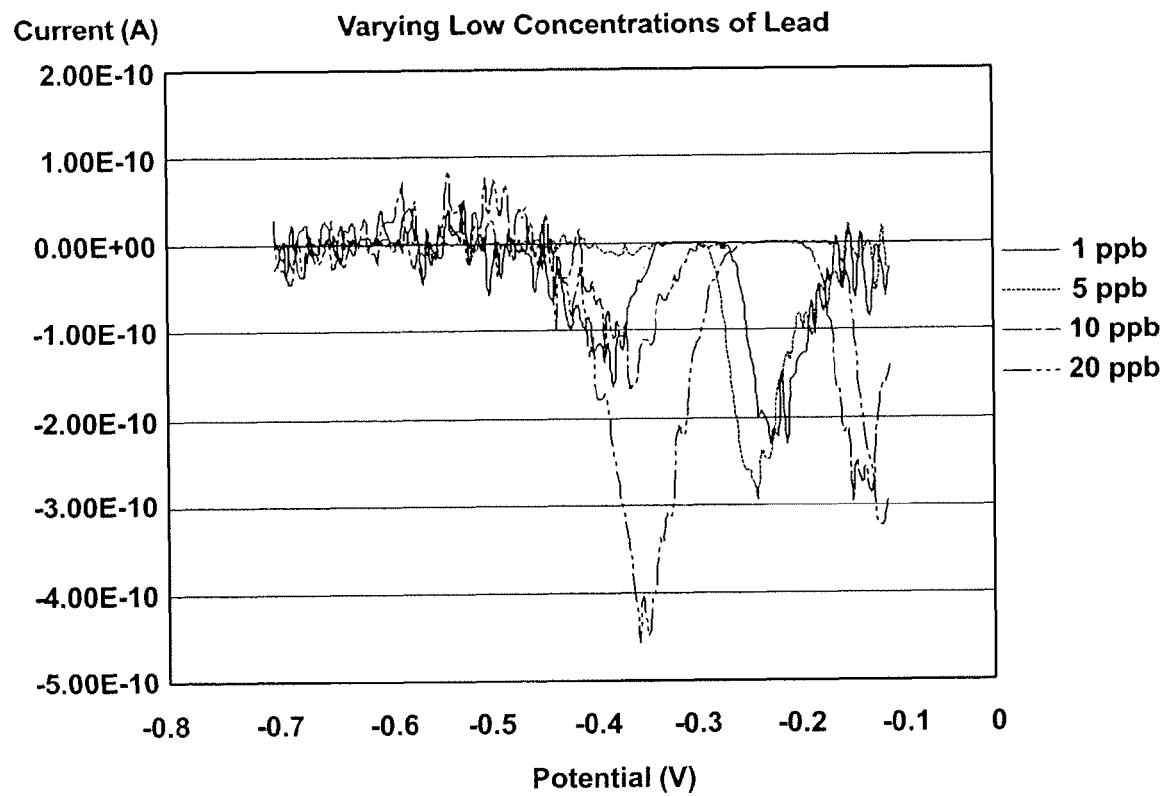
FIGS. 34-36 graphically illustrate results of testing the microelectrodes disclosed herein in Pb ions using anodic stripping voltammetry (ASV)
Figure 35:
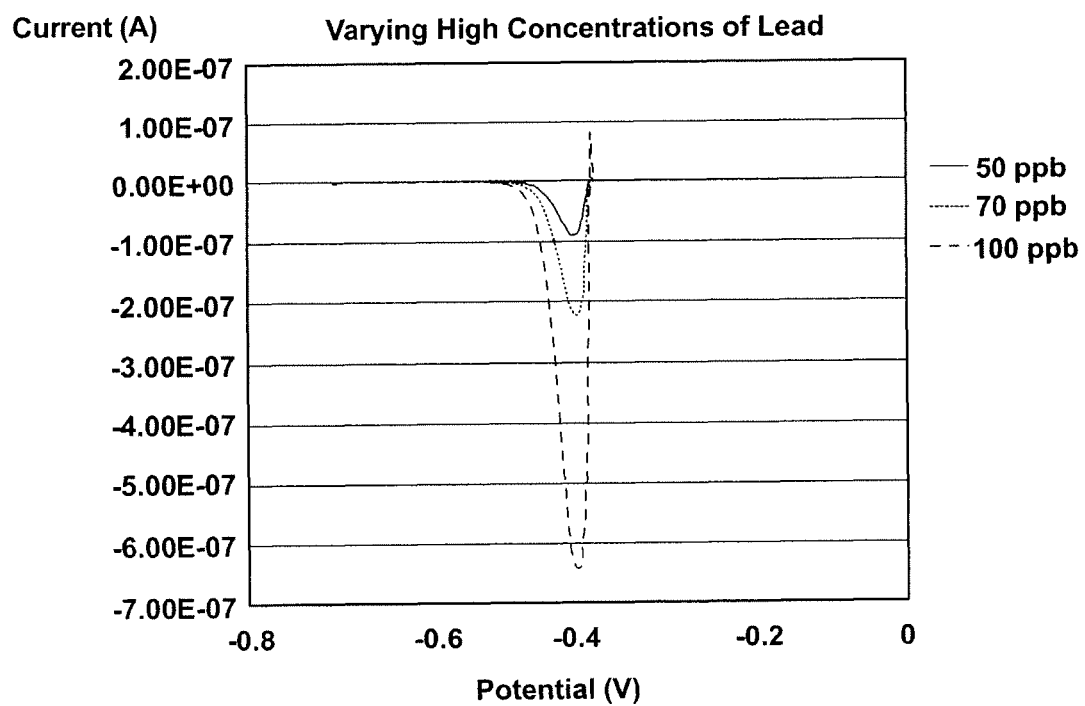
Figure 36:
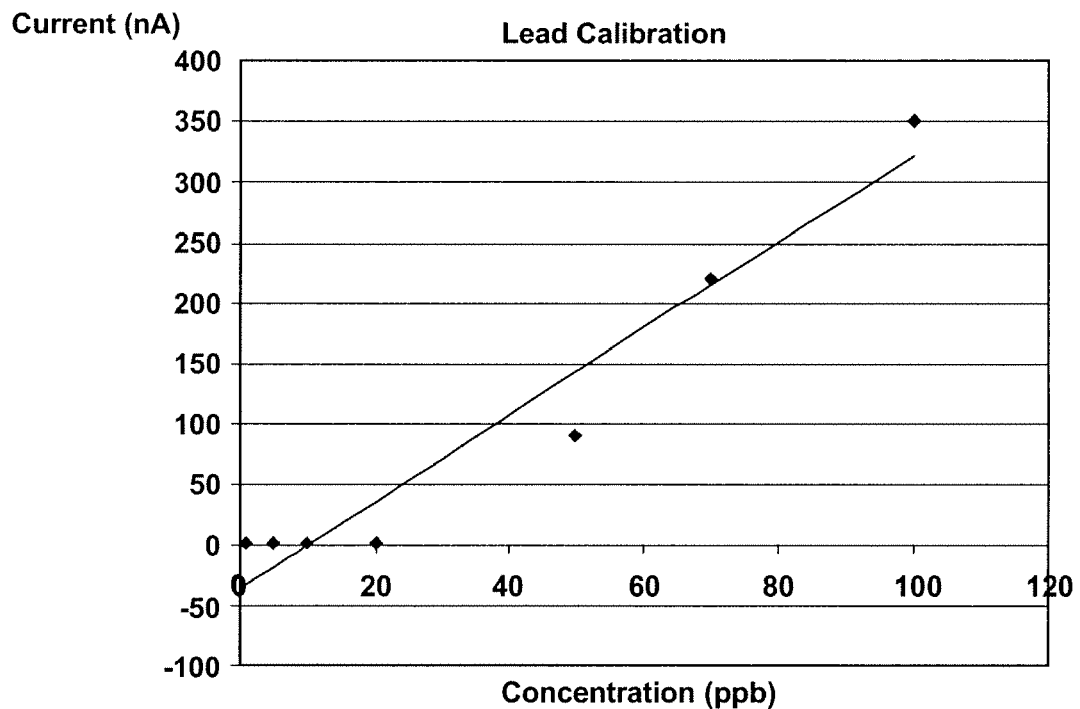

After standardizing and quantifying the microelectrodes, an analysis in water is performed in order to check the calibration of the microelectrodes with known concentrations of solutions. Example tests were performed on Pb and Zn. Preliminary data was also collected on Cu. FIGS. 34-36 graphically illustrate results of testing the microelectrodes disclosed herein in Pb ions using anodic stripping voltammetry (ASV). Absolute values of the peak heights are tabulated corresponding to each concentration. As shown in FIG. 36, there is a distinct linear relationship between concentration and current. Regression statistics corresponding to FIG. 36 are given in Table 2 below.

TABLE 2

| | |
|---|---|
| Slope | 3.588 |
| Intercept | −36.765 |
| R2 | 0.946 |
| Steyx | 35.381 |

Figure 37:
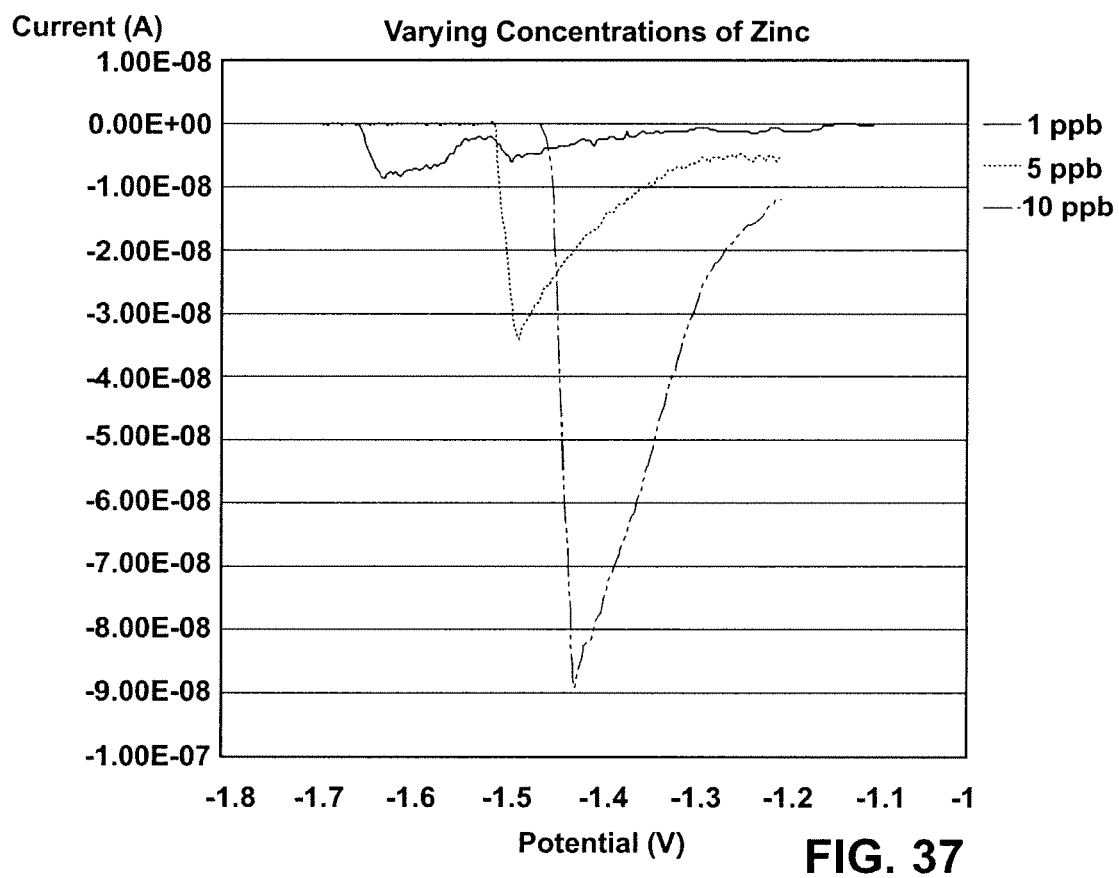
FIGS. 37-39 graphically illustrate results of testing the microelectrodes disclosed herein in Zn ions using ASV.
Figure 38:
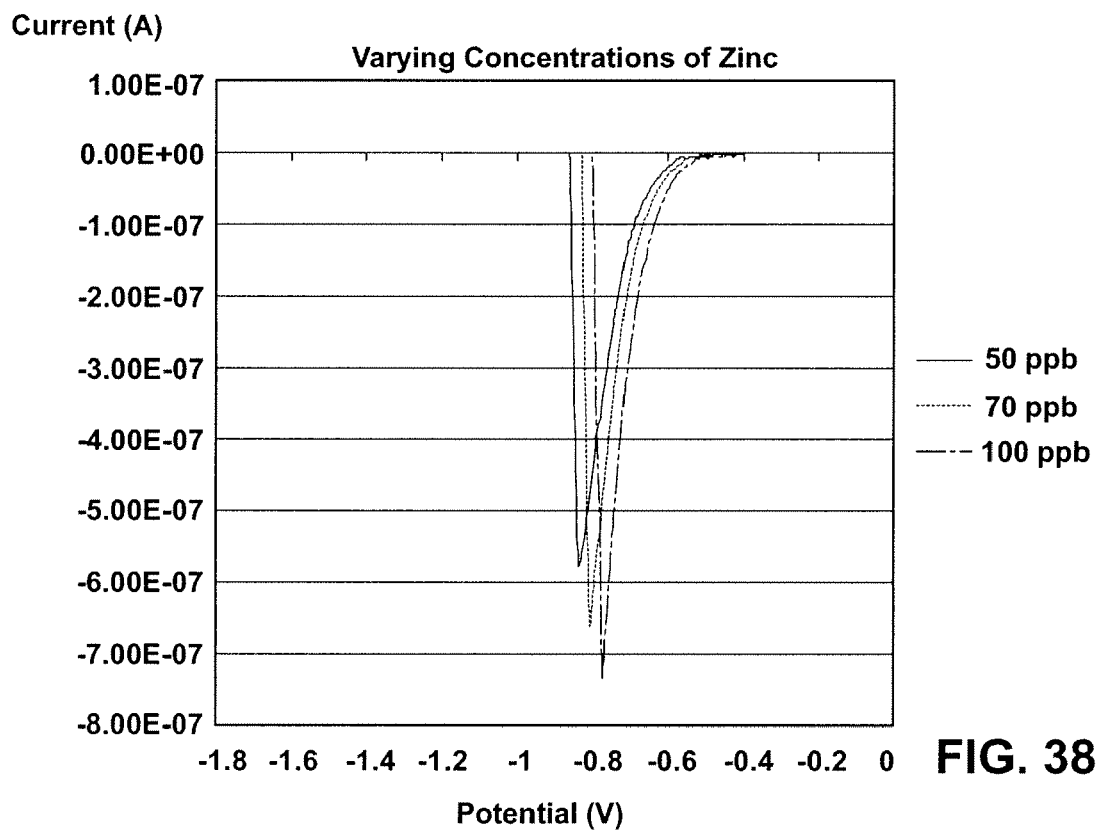
Figure 39:
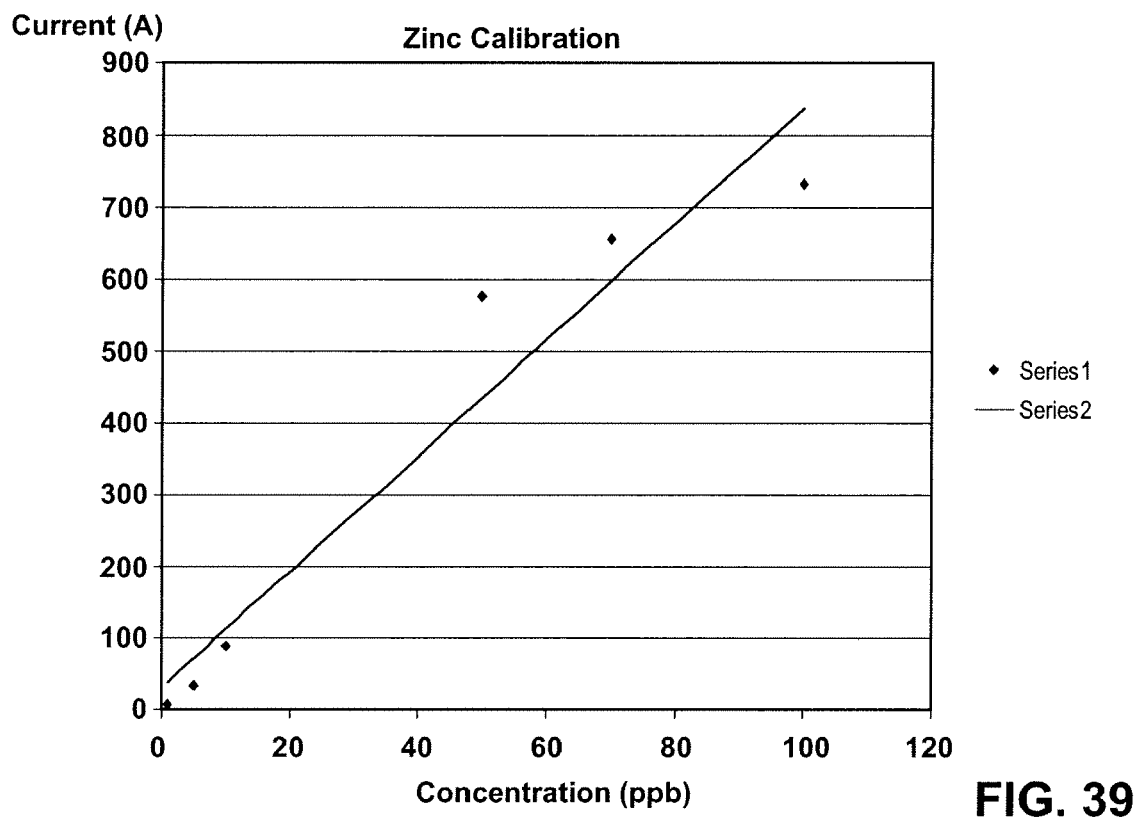

Following the measurement of the Pb ions, Zn was examined in solution. FIGS. 37-39 graphically illustrate the ASV test results for Zn ions. As seen in FIGS. 37 and 38, there is a shift in the characteristic potential data as Zn ion concentration is increased. The cause of this shift has not yet been determined. As with the Pb test results, the peak heights are tabulated with corresponding concentration. As shown in FIG. 39, there is a linear relationship between concentration and current. Regression statistics corresponding to FIG. 39 are given below in Table 3.

TABLE 3

| | |
|---|---|
| Slope | 8.074 |
| Intercept | 31.398 |
| R2 | 0.935 |
| Steyx | 96.993 |

Figure 40:
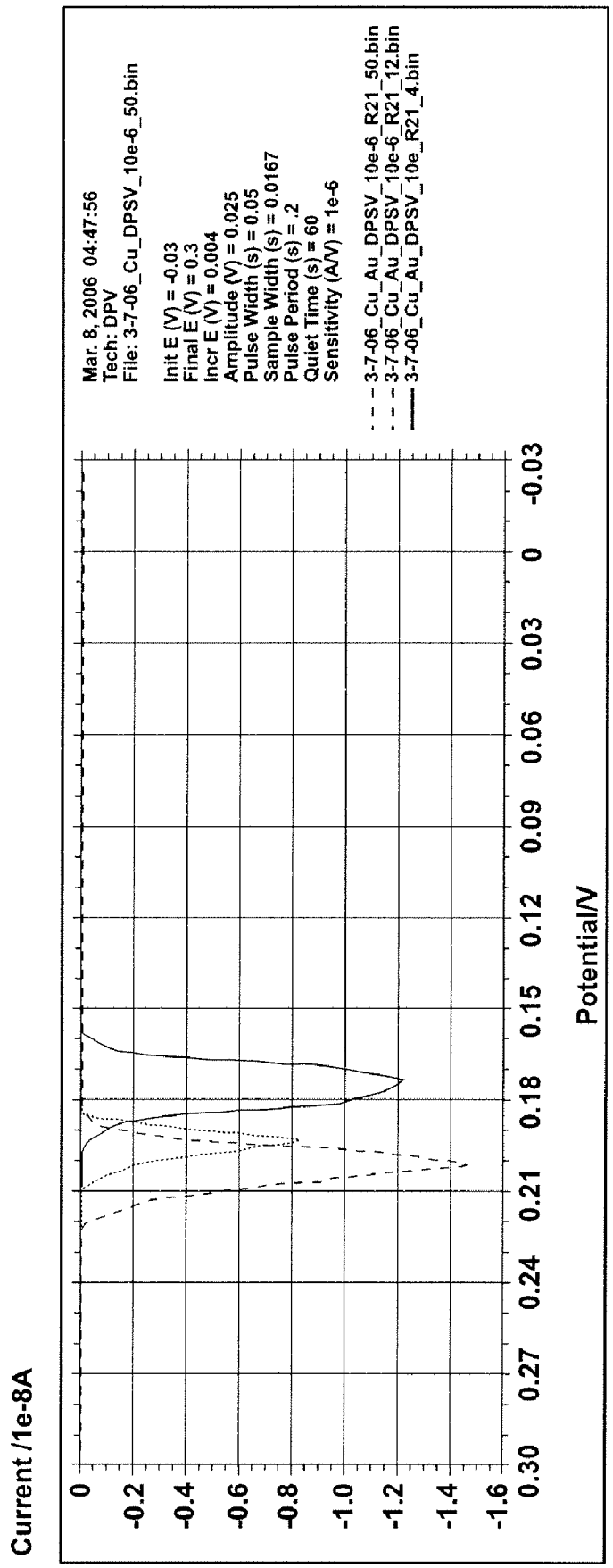
FIG. 40 graphically illustrates results of testing the microelectrodes disclosed herein in Cu ions using ASV.

Preliminary tests were also performed with Cu ions in solution. FIG. 40 graphically illustrates the DPSV test results for the Cu ions. As shown in FIG. 40, the DPSV peaks at approximately 4, 12, and 50 ppb. These results seem to follow the same trend as both Pb and Zn, and similar linear relationships between peak heights and concentrations are expected.

Based on these example experiment results, the microelectrode arrays and methods disclosed herein were proven to be highly selective and sensitive to low concentrations by standardizing them with Potassium Ferric Cyanide solution. Using a DPSV mode of ASV, current/voltage relationships and standard calibrations for Pb, Zn and Cu ions were obtained. The desired linear concentration versus current change for Pb and Zn are shown in FIGS. 36 and 39. Tables 2 and 3 may be used with unknown concentrations of Pb and Zn to quantify the unknown concentrations.

It will be obvious to those having skill in the art that many changes may be made to the details of the above-described embodiments without departing from the underlying principles of the invention. The scope of the present invention should, therefore, be determined only by the following claims.

The invention claimed is:

1. An integrated electrochemical chip comprising:
a microprocessor configured to allow a user to select from among a plurality of available electrochemical techniques for use by the integrated electrochemical chip to measure an ion concentration in a solution;
a function generator controlled by the microprocessor to selectively generate a waveform based on the user-selected electrochemical technique; and
a potentiostat configured to generate and measure a current in the solution through a plurality of electrodes according to the user-selected electrochemical technique, wherein the potentiostat comprises:
a control amplifier configured to provide a current through a first electrode and a second electrode so as to maintain a predetermined voltage between the second electrode and a third electrode; and
a current amplifier configured to measure the current provided through the first electrode and the second electrode,
wherein the current amplifier is configured to measure the current throughout an entire range comprising approximately 100 pA to approximately 2 mA.

2. The integrated electrochemical chip of claim 1, wherein the control amplifier is further configured to prevent the third electrode from polarizing.

3. The integrated electrochemical chip of claim 1, further comprising an electrically conductive guard configured to reduce a portion of the current measured by the current amplifier that is attributable to a leakage current through the third electrode.

4. The integrated electrochemical chip of claim 1, wherein the current amplifier comprises a voltage meter referenced to ground.

5. The integrated electrochemical chip of claim 1, wherein the current amplifier comprises a potentiometer controlled by a microprocessor to selectively adjust the gain of the current amplifier.

6. The integrated electrochemical chip of claim 1, wherein the potentiostat further comprises a lock-in amplifier comprising a phase sensitive detector configured to multiply a phase shifted reference signal by the current, the lock-in amplifier configured to reduce the current's noise.

7. The integrated electrochemical chip of claim 1, wherein the plurality of available electrochemical techniques comprises square wave voltammetry, cyclic voltammetry, linear sweep voltammetry, differential-pulse voltammetry, and normal-pulse voltammetry.

8. The integrated electrochemical chip of claim 1, wherein the function generator comprises a direct digital frequency synthesizer (DDFS).

9. The integrated electrochemical chip of claim 8, wherein the DDFS comprises a phase accumulator.

10. The integrated electrochemical chip of claim 9, wherein the phase accumulator comprises:
an N-bit phase register controlled by a clock signal comprising a clock frequency; and
an N-bit adder comprising:
a first input for a frequency control word from a microprocessor; and
a second input for feedback from the N-bit phase register,
wherein the contents of the N-bit phase register increase by the value of the frequency control word at the end of a cycle of the clock signal.

11. The integrated electrochemical chip of claim 10, wherein a frequency of the waveform is selectively controlled by the frequency control word.

12. The integrated electrochemical chip of claim 11, wherein the frequency of the waveform and a frequency resolution of the waveform are further based on the clock frequency and the N number of bits.

13. The integrated electrochemical chip of claim 9, wherein the DDFS further comprises:
a memory configured to receive an output of the phase accumulator;
a digital-to-analog converter configured to receive an output of the memory; and
a low-pass filter configured to remove harmonic distortion from an output of the digital-to-analog converter.

14. The integrated electrochemical chip of claim 1, wherein the function generator comprises:
a first Schmitt circuit configured to generate a square wave;
a second Schmitt circuit configured to generate a triangle wave; and
a summing amplifier circuit configured to combine the square wave and the triangle wave.

15. The integrated electrochemical chip of claim 14, wherein at least one of the first Schmitt circuit and the second Schmitt circuit comprises a constant current source.

16. An integrated electrochemical chip comprising:
a microprocessor;
a function generator controlled by the microprocessor to selectively generate a waveform; and
a potentiostat integrated with the microprocessor and the function generator, the potentiostat configured to generate and measure a current in a solution, wherein the potentiostat is configured to generate and measure the current throughout an entire range comprising about 100 pA to about 2 mA.

17. The integrated electrochemical chip of claim 16, wherein the potentiostat comprises a control amplifier configured to provide the current through a first electrode and a second electrode so as to maintain a predetermined voltage between the second electrode and a third electrode.

18. The integrated electrochemical chip of claim 17, wherein the control amplifier is further configured to prevent the third electrode from polarizing.

19. The integrated electrochemical chip of claim 17, wherein the potentiostat further comprises a current amplifier configured to measure the current provided through the first electrode and the second electrode.

20. The integrated electrochemical chip of claim 19, further comprising an electrically conductive guard configured to reduce a portion of the current measured by the current amplifier that is attributable to a leakage current through the third electrode.

21. The integrated electrochemical chip of claim 19, wherein the current amplifier comprises a voltage meter referenced to ground.

22. The integrated electrochemical chip of claim 19, wherein the current amplifier comprises a potentiometer controlled by a microprocessor to selectively adjust the gain of the current amplifier.

23. The integrated electrochemical chip of claim 16, wherein the potentiostat further comprises a lock-in amplifier comprising a phase sensitive detector configured to multiply a phase shifted reference signal by the current, the lock-in amplifier configured to reduce the current's noise.

24. The integrated electrochemical chip of claim 16, wherein the waveform is specified by an electrochemical technique selected from the group comprising square wave voltammetry, cyclic voltammetry, linear sweep voltammetry, differential-pulse voltammetry, and normal-pulse voltammetry.

25. The integrated electrochemical chip of claim 16, wherein the function generator comprises a direct digital frequency synthesizer (DDFS).

26. The integrated electrochemical chip of claim 25, wherein the DDFS comprises a phase accumulator.

27. The integrated electrochemical chip of claim 26, wherein the phase accumulator comprises:
    an N-bit phase register controlled by a clock signal comprising a clock frequency; and
    an N-bit adder comprising:
        a first input for a frequency control word from a microprocessor; and
        a second input for feedback from the N-bit phase register,
    wherein the contents of the N-bit phase register increase by the value of the frequency control word at the end of a cycle of the clock signal.

28. The integrated electrochemical chip of claim 27, wherein a frequency of the waveform is selectively controlled by the frequency control word.

29. The integrated electrochemical chip of claim 28, wherein the frequency of the waveform and a frequency resolution of the waveform are further based on the clock frequency and the N number of bits.

30. The integrated electrochemical chip of claim 26, wherein the DDFS further comprises:
    a memory configured to receive an output of the phase accumulator;
    a digital-to-analog converter configured to receive an output of the memory; and
    a low-pass filter configured to remove harmonic distortion from an output of the digital-to-analog converter.

* * * * *